US006231557B1

(12) United States Patent
Krautkramer et al.

(10) Patent No.: US 6,231,557 B1
(45) Date of Patent: May 15, 2001

(54) ABSORBENT PRODUCT CONTAINING AN ELASTIC ABSORBENT COMPONENT

(75) Inventors: Candace Dyan Krautkramer, Greenville; Rob David Everett, Appleton; Toan Thanh LeMinh, Greenville; Debra Jean McDowall, Neenah; Hoa La Wilhelm, Appleton; David Louis Zenker, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/387,950

(22) Filed: Sep. 1, 1999

(51) Int. Cl.[7] ....................................................... A61F 13/15
(52) U.S. Cl. ............................... 604/385.16; 604/385.01; 604/385.22; 604/385.23

(56) References Cited

U.S. PATENT DOCUMENTS

| 3,901,236 | 8/1975 | Assarsson et al. . |
| 4,076,663 | 2/1978 | Masuda et al. . |

(List continued on next page.)

FOREIGN PATENT DOCUMENTS

| 0 217 032 A2 | 4/1987 | (EP) . |
| 0 321 985 A2 | 6/1989 | (EP) . |
| 0 450 541 A2 | 10/1991 | (EP) . |
| 0 780 108 A1 | 6/1997 | (EP) . |
| 2140471 | 11/1984 | (GB) . |
| 2 297 491 A1 | 8/1996 | (GB) . |
| WO 93/01786 | 2/1993 | (WO) . |
| WO 93/05742 | 4/1993 | (WO) . |
| WO 94/02094 | 2/1994 | (WO) . |
| WO 95/16425 A2 | 6/1995 | (WO) . |
| WO 96/10978 | 4/1996 | (WO) . |
| WO 96/16624 | 6/1996 | (WO) . |
| WO 96/32084 A1 | 10/1996 | (WO) . |
| WO 97/01996 | 1/1997 | (WO) . |
| WO 98/08476 | 3/1998 | (WO) . |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

American Society for Testing Materials (ASTM) Designation: D 3039/D 3039M–95a, "Standard Test Method for Tensile Properties of Polymer Matrix Composite Materials," pp. 99–109, published Oct. 1995.

Hull, Mark, H.B. Fuller Company, "West Strength and Core Integrity in Disposables," *Nonwovens World*, Insight 97 Conference Issue, Fall 1997, pp. 65–66,68–70, and 72.

*Primary Examiner*—John G. Weiss
*Assistant Examiner*—Paul Shanoski

(57) ABSTRACT

An absorbent article (10) has a longitudinal direction (26), a lateral, transverse direction (24), an article front portion (14), an article back portion (12), and an intermediate portion (16) interconnecting the front and back portions. The article includes an elastomerically stretchable backsheet member (30), a liquid-permeable topsheet layer (28), and an elastomerically stretchable retention portion (48) sandwiched between the backsheet member (30) and the topsheet layer (28). The topsheet layer can be elastomerically stretchable, and the absorbent article (10) can also provide a selected combination of physical properties, such as a composite-article elongation-at-peak-load value which is at least about 50 percent.

16 Claims, 8 Drawing Sheets

U.S. PATENT DOCUMENTS

| | | |
|---|---|---|
| 4,100,324 | 7/1978 | Anderson et al. . |
| 4,286,082 | 8/1981 | Tsubakimoto et al. . |
| 4,429,001 | 1/1984 | Kolpin et al. . |
| 4,663,220 | 5/1987 | Wisneski et al. . |
| 4,699,823 | 10/1987 | Kellenberger et al. . |
| 4,704,116 | 11/1987 | Enloe . |
| 4,741,949 * | 5/1988 | Morman et al. ................. 428/224 |
| 4,753,646 | 6/1988 | Enloe . |
| 4,822,668 | 4/1989 | Tanaka et al. . |
| 4,902,463 | 2/1990 | Tenaka et al. . |
| 4,916,005 | 4/1990 | Lippert et al. . |
| 4,931,005 | 6/1990 | Tanaka et al. . |
| 4,935,021 | 6/1990 | Huffman et al. . |
| 4,938,753 | 7/1990 | Van Gompel et al. . |
| 5,019,073 | 5/1991 | Roessler et al. . |
| 5,226,992 | 7/1993 | Morman . |
| 5,316,837 * | 5/1994 | Cohen ............................ 428/285 |
| 5,320,891 * | 6/1994 | Levy et al. ..................... 428/108 |
| 5,366,452 | 11/1994 | Widlund et al. . |
| 5,399,219 | 3/1995 | Roessler et al. . |
| 5,451,219 | 9/1995 | Suzuki et al. . |
| 5,486,166 | 1/1996 | Bishop et al. . |
| 5,490,846 | 2/1996 | Ellis et al. . |
| 5,540,796 | 7/1996 | Fries . |
| 5,560,878 | 10/1996 | Dragoo et al. . |
| 5,562,650 | 10/1996 | Everett et al. . |
| 5,595,618 | 1/1997 | Fries et al. . |
| 5,599,585 * | 2/1997 | Cohen ............................ 427/250 |
| 5,601,542 | 2/1997 | Melius et al. . |
| 5,605,735 | 2/1997 | Zehner et al. . |
| 5,624,429 | 4/1997 | Long et al. . |
| 5,645,542 | 7/1997 | Anjur et al. . |
| 5,650,214 | 7/1997 | Anderson et al. . |
| 5,662,634 | 9/1997 | Yamamoto et al. . |
| 5,665,803 * | 9/1997 | Nohr et al. ..................... 524/267 |
| 5,683,374 | 11/1997 | Yamamoto et al. . |
| 5,804,286 * | 9/1998 | Quantrille et al. ............. 428/198 |
| 5,820,973 | 10/1998 | Dodge, II et al. . |
| 5,858,515 | 1/1999 | Stokes et al. . |
| 5,904,675 | 5/1999 | Laux et al. . |
| 5,910,136 * | 6/1999 | Hetzler et al. ................. 604/367 |

* cited by examiner

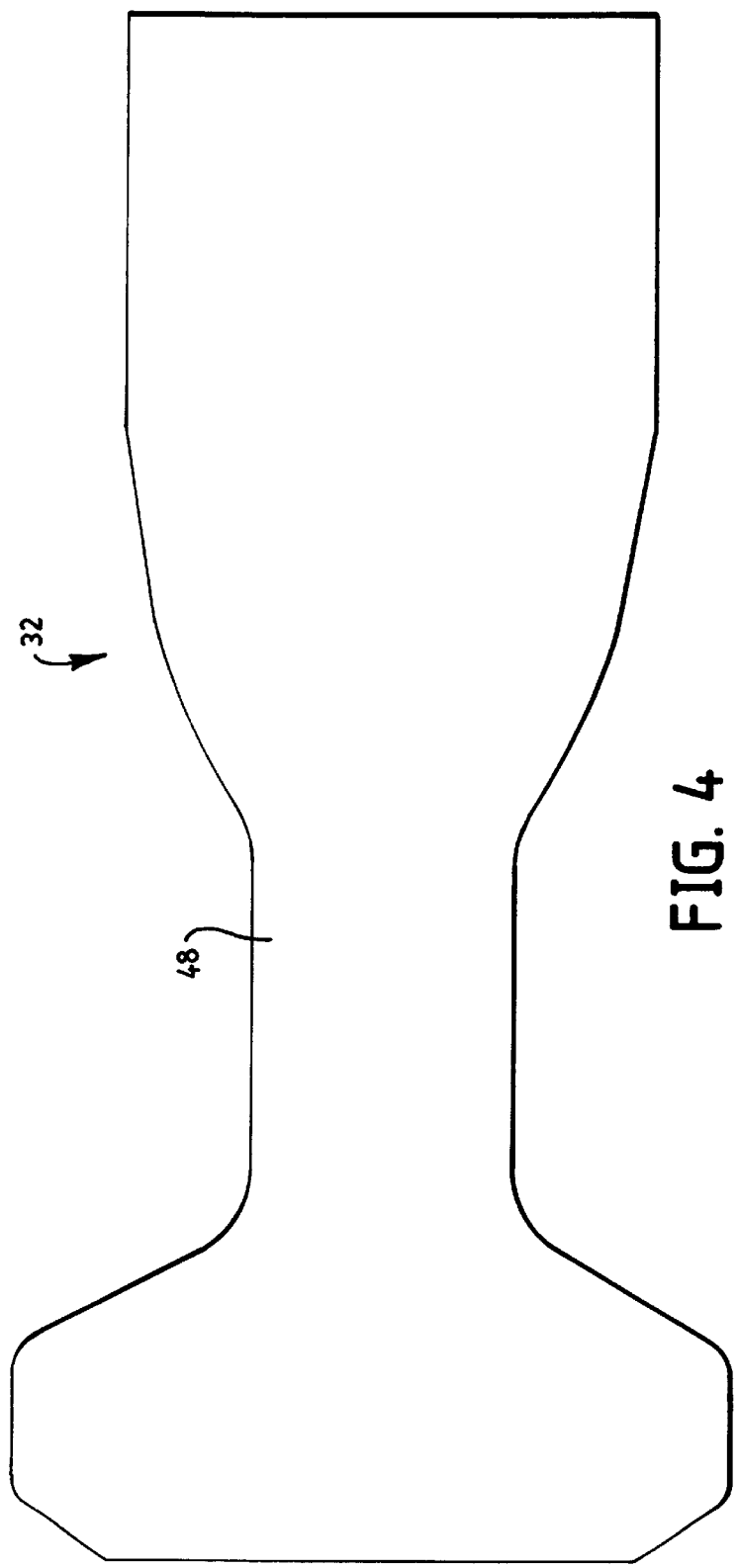

ABSORBENT PRODUCT CONTAINING AN ELASTIC ABSORBENT COMPONENT

FIELD OF THE INVENTION

The present invention relates to absorbent articles. More particularly, the present invention relates to an absorbent article which includes an elastically stretchable absorbent structure. The absorbent article can exhibit improved levels of softness, fit and leakage resistance.

BACKGROUND OF THE INVENTION

The performance objectives of disposable absorbent articles, such as infant diapers, include leakage prevention, dry feel to the wearer, and a comfortable fit throughout the product life. Accordingly, absorbent articles have typically contained an absorbent core to provide liquid handling and other absorbent functionalities required to meet the product performance objectives. The absorbent core of a conventional absorbent article has typically been composed of absorbent fibers, and a superabsorbent material has typically been combined with the absorbent fibers to increase the liquid absorbent capacity. The absorbent core has been formed in a substantially rectangular shape. The absorbent core has also been formed in an hourglass shape, a T-shape, or similar configuration with a reduced absorbent width in the central crotch region for improved fit and comfort.

Conventional absorbent cores have incorporated dry-formed materials which have been produced with various conventional airlaying techniques. The airlaying techniques have typically laid an air-directed mixture of absorbent fibers and superabsorbent to form a web of the absorbent material.

Conventional absorbent cores have also incorporated wet-formed materials which have been produced with various wet-laying techniques. The wet-laying techniques have typically formed an absorbent web produced from a precursor material composed of a mixture of fibers and superabsorbent particles combined with water or other aqueous liquid. A particular wet-laying technique has processed the precursor material into a foam, and the foam has then been employed to form the desired web of absorbent material.

Such conventional absorbent cores have been elasticized by various techniques to provide elastomeric stretchability and better conformance to the wearer's body. In addition, the absorbent articles have incorporated elastomerically stretchable outercovers to provide better appearance and fit. Such elastomerically stretchable outercovers have included composites composed of nonwoven fabric webs and elastomeric webs. The elastomeric webs may be elastomeric films or elastomeric fabrics, and the entire outercover may be elastomerically stretchable.

Such conventional absorbent article, however, have not provided desired levels of stretchability, conformance and integrity. For example, the conventional absorbent articles have not provided a desired combination of relative stretchability between the outercover and the absorbent structure. The conventional absorbent articles also have not provided a desired combination of stress and strain characteristics between the outercover and the absorbent structure, and between the overall article and the absorbent structure. As a result, the conventional absorbent articles have exhibited unsightly appearance, poor fit and conformance, excessive gapping between the article and the wearer's body, and excessive leakage.

Consequently, there remains a need for absorbent structures which can provide desired combinations of flexibility, integrity, conformance to the wearer's body and improved leakage resistance.

BRIEF DESCRIPTION OF THE INVENTION

Generally stated, the present invention provides an absorbent article having a longitudinal direction, a lateral, transverse direction, a first portion, a second portion, and an intermediate portion interconnecting the first and second portions. The article includes a stretchable backsheet member, a liquid-permeable topsheet layer, and a stretchable retention portion sandwiched between the backsheet member and the topsheet layer. In particular aspects, the absorbent article can include a stretchable topsheet layer, and in other aspects, the article can provide a selected elongation-at-peak-load value. In still other aspects, the backsheet member, the retention portion and the article can have a selected combination of relative properties. In further aspects, the backsheet member can be substantially liquid-impermeable when stretched to a selected backsheet elongation.

The present invention can provide a distinctive absorbent article which can exhibit desirable physical properties, such as softness, flexibility, conformance, trim appearance, reduced gapping and reduced leakage during use. The article can also include an absorbent structure which exhibits desirable physical properties, such as improved softness, flexibility, durability, conformance and stretchability. As a result, the articles and absorbent structures of the invention can provide increased strength, improved fit, reduced leakage, and reduced clumping, bunching or sagging during use.

BRIEF DESCRIPTION OF THE DRAWINGS

The present invention will be more fully understood and further advantages will become apparent when reference is made to the following detailed description of the invention and the drawings, in which:

FIG. 4 representatively shows a top, plan view of a multiple-layer absorbent retention portion which can be employed with the present invention;

DETAILED DESCRIPTION OF THE INVENTION

The various aspects and embodiments of the invention will be described in the context of a disposable absorbent
} article, such as a disposable diaper. It is, however, readily apparent that the present invention could also be employed with other articles, such as gowns, covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

Figure 1:
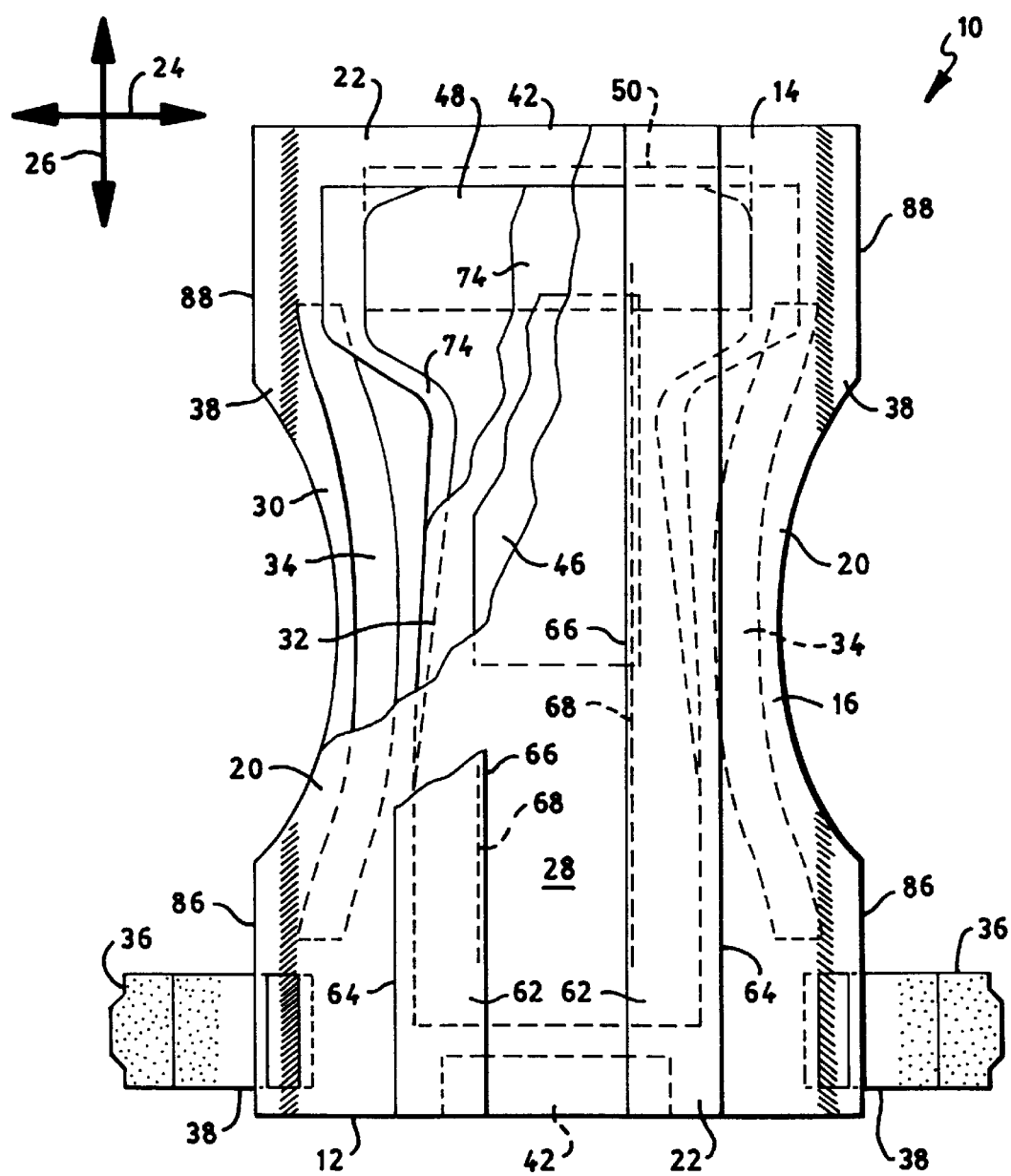
FIG. 1 representatively shows a partially cut-away, top view of a diaper article which incorporates the fastening system of the invention.
Figure 2:
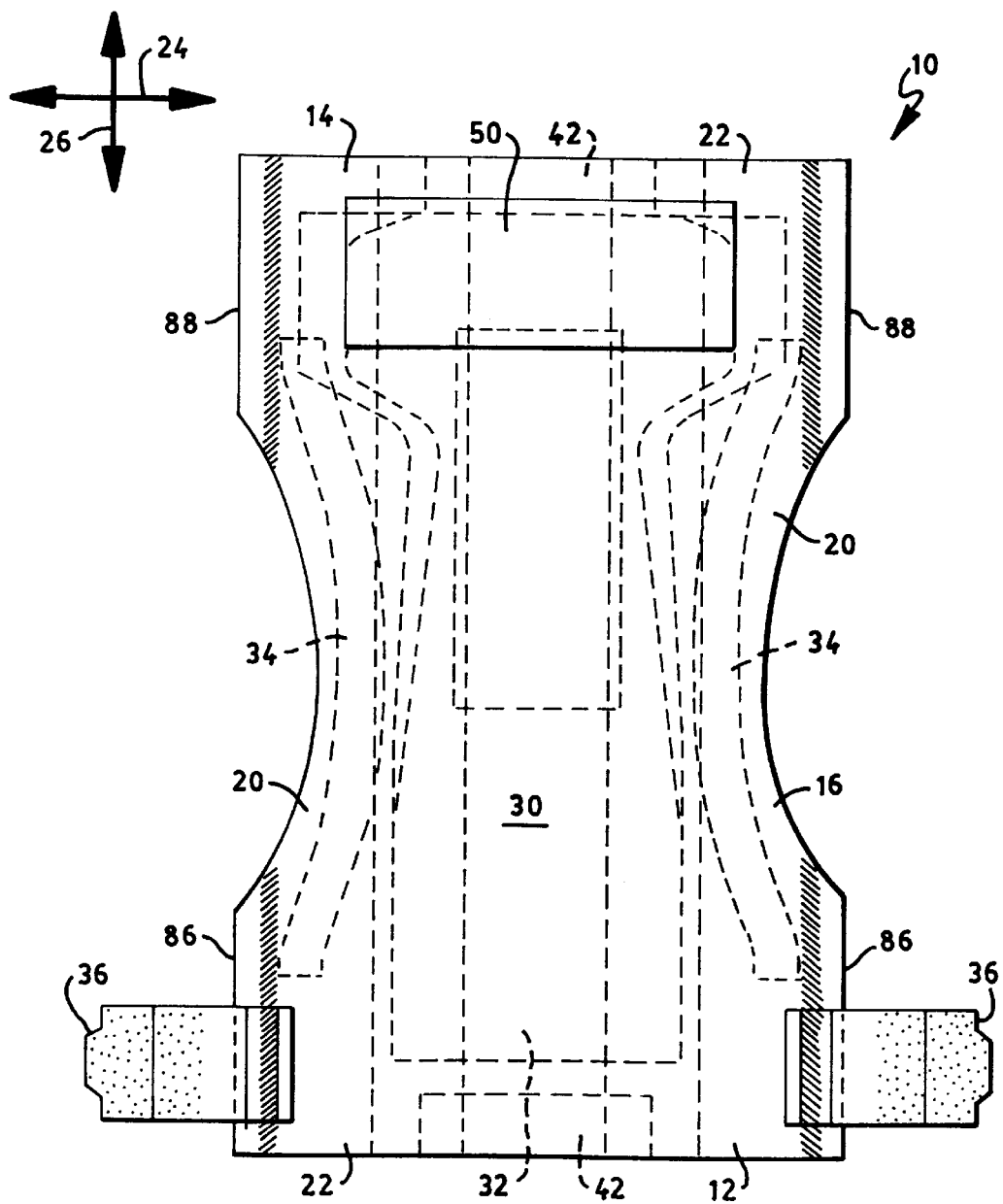
FIG. 2 representatively shows a plan view of the outward side of the article representatively shown in FIG. 1.
Figure 3:
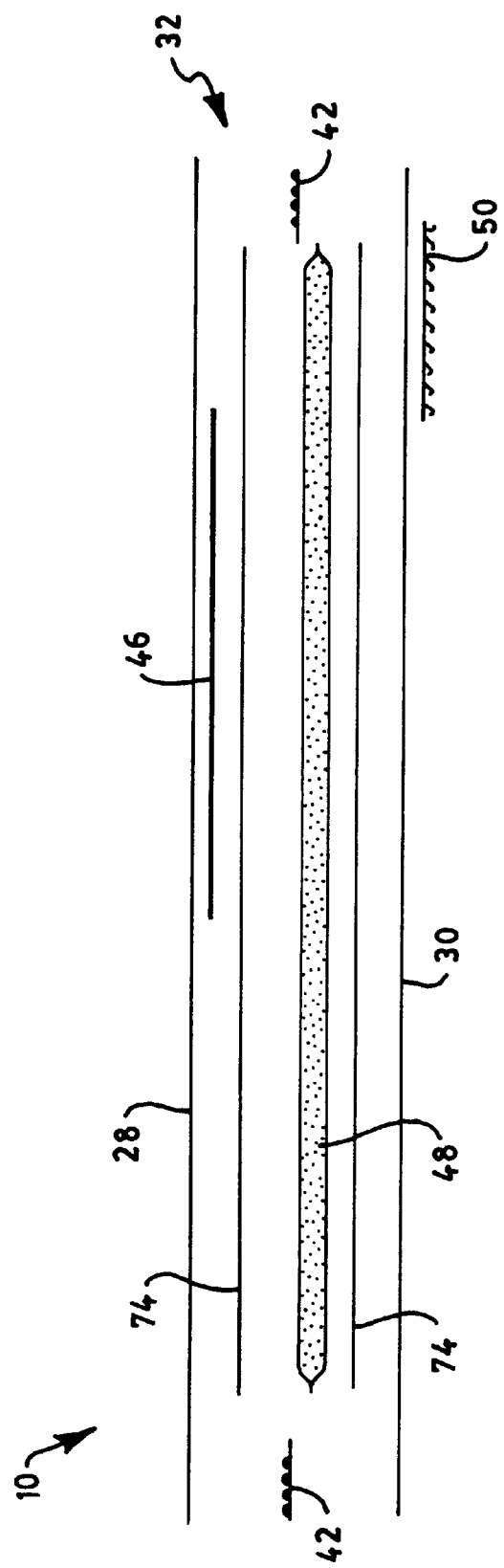
FIG. 3 representatively shows an expanded, schematic, longitudinal cross-sectional view of the article representatively shown in FIG. 1.

With reference to FIGS. 1, 2 and 3, an article, such as the representatively shown diaper 10, has a lengthwise, longitudinal direction 26, a lateral, transverse cross-direction 24, a first article portion, such as a front portion 14, a second article portion, such as a back portion 12, and an intermediate portion 16 interconnecting the first and second portions. In particular configurations, the front and back portions may provide front and back waistband portions of the article. The article includes a substantially liquid-impermeable, stretchable backsheet member 30, a liquid-permeable topsheet layer 28, and a stretchable retention portion 48 sandwiched between the backsheet member 30 and the topsheet layer 28. The backsheet member 30 and retention portion 48 are desirably elastomerically stretchable. The absorbent article can provide a selected elongation-at-peak-load value, such as an article elongation-at-peak-load value which is at least about 50 percent. Additionally, the backsheet member 30 can be substantially liquid-impermeable when stretched to a selected backsheet elongation, such as a backsheet elongation of at least about 45 percent. In particular aspects, the topsheet layer 28 is also stretchable, and desirably, is elastomerically stretchable.

In its various aspects, the invention can provide a distinctive absorbent article which can exhibit desirable physical properties, such as softness, flexibility, conformance, trim appearance, reduced gapping and reduced leakage. The article can include an absorbent structure, particularly a retention portion 48, which exhibits desirable physical properties, such as improved softness, flexibility, durability, conformance and stretchability. As a result, the absorbent structures and articles of the invention can provide increased strength, improved fit, reduced leakage, and reduced clumping, bunching or sagging during use.

The article of the invention can, for example, be a garment provided by the representatively shown disposable diaper 10. In desired aspects of the invention, the first article portion can, for example, provide a first, rear or back waistband portion 12, and the second article portion can provide a second, front waistband portion 14. In addition, the article can have an intermediate or crotch portion 16 which interconnects between the first and second waistband portions 12 and 14, respectively. The diaper can further include a backsheet member 30, a liquid permeable topsheet layer 28 connected and assembled in facing relation with the backsheet member, and an absorbent structure, such as a structure which includes an absorbent body 32. The absorbent structure is sandwiched between the backsheet and topsheet layers, and is operably held therebetween.

In addition, a fastening system, such as the system including fasteners 36, may be employed to interconnect the first waistband portion 12 with the second waistband portion 14 to hold the article on a wearer.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing zone member 50 which is disposed on the outward surface of the article. In the configuration shown in FIGS. 1, 2 and 3, for example, the landing member 50 is disposed on the outward surface of the backsheet member 30. The liquid permeable topsheet layer 28 is superposed in facing relation with the backsheet member 30, and the absorbent body 32 is operably connected and affixed between the backsheet member 30 and topsheet layer 28.

FIGS. 1 and 2 show typical plan views of the representative disposable diaper 10 in its generally flat-out, uncontracted state (i.e., with substantially all elastic induced gathering and contraction removed). In FIG. 1, the bodyside surface of the diaper which contacts the wearer is facing the viewer, and portions of the structure are partially cut away to more clearly show the interior construction of the diaper article. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article is configured to face away from the wearer's body when the article is placed about the wearer.

The diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with an appointed storage or retention portion 48 of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995; in U.S. patent application Ser. No. 286,086 of D. Fries, entitled A PROCESS FOR ASSEMBLING ELASTICIZED EAR PORTIONS and filed Aug. 3, 1994 which corresponds to U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 which corresponds to U.S. Pat. No. 5,595,618. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet layer and backsheet member may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, a composite laminate, or other flexible, substantially liquid-impermeable material. As used in the present specification, the term "flexible" refers to materials which are compliant and which will readily conform to the general shape and contours of the wearer's body. The backsheet 30 substantially prevents the exudates contained in absorbent body 32 from wetting articles, such as bedsheets and overgarments, which contact the diaper 10. In particular embodiments of the invention, the backsheet 30 can include a 0.4 osy (13.6 g/m$^2$) basis weight of G2760 KRATON elastomer strands adhesively laminated with a 0.3 g/m$^2$ add-on of adhesive between two facings. Each facing can be composed of a thermal point bonded bicomponent spunbond nonwoven fibrous web having a 0.7 osy (23.7 g/m2) basis weight. The adhesive is similar to an adhesive which is supplied by AtoFindley Adhesive and designated as H2525 A, and the elastomer strands are placed and distributed to provide approximately 12 strands of KRATON elastomer per inch (2.54 cm) of lateral width of the backsheet material.

Alternative constructions of the backsheet member may comprise a woven or non-woven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 g/m$^2$) polypropylene spunbond material (2 denier fibers). A material of this type forms the outercover of a HUGGIES SUPREME disposable diaper, which is commercially available from Kimberly-Clark Corporation. The backsheet 30 typically provides the outer cover of the article. Optionally, however, the article may include a separate outer cover component member which is additional to the backsheet.

The backsheet 30 may alternatively include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 30 or the containment flaps 62 are configured to be permeable to gas while having a resistance and limited permeability to aqueous liquid, the liquid resistant or substantially liquid-impermeable material can have a construction which is capable of supporting a selected hydrohead of at least about 45 cm of water substantially without leakage therethrough. A suitable technique for determining the resistance of a material to liquid penetration and the capability of the material to support a hydrohead of water without substantial leakage is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

Desirably, the backsheet member 30 is substantially elastomerically stretchable. The backsheet member may, for example, be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch Bonded Laminates (SBL) and Neck Bonded Laminates (NBL) are examples of elastomeric composites. Nonwoven fabrics are any web of material which has been formed without the use of textile weaving processes which produce a structure of individual fibers which are interwoven in an identifiable repeating manner. Examples of suitable materials are Spunbond-Meltblown fabrics, Spunbond-Meltblown-Spunbond fabrics, Spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from E. I. DuPont de Nemous located in Wilmington, Del.), KRATON elastomer (available from Shell Chemical Company located in Houston, Tex.), or strands of LYCRA elastomer (available from E. I. DuPont de Nemous located in Wilmington, Del.), or the like, as well as combinations thereof. These backsheet member 30 may include materials that have elastomer properties through a mechanical process, printing process, heating process, or chemical treatment. For examples such materials may be apertured, creped, neck-stretched, heat activated, embossed, and micro-strained; and may be in the form of films, webs, and laminates.

In desired arrangements, the backsheet member 30 can have a selected resistance to liquid penetration when stretched to an elongation of 45%. In particular aspects, the backsheet member can have a construction which is capable of supporting a hydrohead of at least about 10 cm of water substantially without leakage therethrough. The backsheet member can alternatively support a hydrohead of at least about 14 cm, and optionally, can support a hydrohead of at least about 20 cm to provide improved performance.

In further aspects of the invention, the backsheet member 30 can be substantially liquid-impermeable and support a hydrohead of at least about 45 cm when stretched to a backsheet elongation which is at least a minimum of about 45%. Alternatively, the backsheet can be substantially liquid-impermeable when stretched to a backsheet elongation which is at least about 47%, and optionally, is at least about 50% to provide improve performance. In other aspects, the backsheet can be substantially liquid-impermeable when stretched to a backsheet elongation of up to about 60%. The backsheet can be substantially liquid-impermeable when stretched to a backsheet elongation which is alternatively up to about 75%, and optionally, is up to about 100%, or more, to provide improved performance.

A suitable technique for determining the resistance of a material to liquid penetration and the capability of the material to support a hydrohead of water without substantial leakage can incorporate Federal Test Method Standard FTMS 191 Method 5514, 1978, or an equivalent thereof, as described in the Modified Hydrohead For Stretched Materials Testing section of the Procedures portion of the present disclosure.

In other aspects, the backsheet member 30 can have a backsheet elongation-at-peak-load value which is at least a minimum of about 45%, and desirably, is at least about 50%. The backsheet elongation-at-peak-load value can alternatively be at least about 55%, and optionally, can be at least about 75% to provide improved performance. Further configurations of the backsheet member can provide a backsheet elongation-at-peak-load value of at least about 100% to further improve performance. In other aspects, the backsheet elongation-at-peak-load value can be up to a maximum of about 400%, or more. The backsheet elongation-at-peak-load value can alternatively be up to about 300%, and optionally, can be up to about 200%, to provide improved benefits.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may include a meltblown web, a spunbonded web, or a bonded-carded-web composed of the desired fibers. The various fabrics can be composed of natural fibers, synthetic fibers or combinations thereof.

For the purposes of the present disclosure, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, the topsheet 28 can be a nonwoven, spunbond polypropylene fabric composed of about 2 to 3 denier fibers formed into a web having a basis weight of about 12 $g/m^2$ which is necked approximately 60%. Strands of about 9 $g/m^2$ KRATON G2760 elastomer material placed eight strands per inch (2.54 cm) are adhered to the necked spunbond material. The fabric can be surface treated with an operative amount of surfactant, such as about 0.6% AHCOVEL Base N62 surfactant, available from ICI Americas, a business having offices located in Wilmington, Del. The surfactant can be applied by any conventional means, such as spraying, printing, brush coating or the like.

In particular aspects, the bodyside liner or topsheet layer may be comprised of polymer fibers, networks, laminates, liquid permeable films, cellulosic fibers, rayon, water swellable gels, and elastomeric materials, as well as combinations thereof. Suitable materials for the topsheet layer can include meltblown webs, airlaid webs, spunbond webs, or bonded-carded webs of synthetic continuous or discrete polymer fibers and/or natural fibers, a pattern bonded spunbonded web, airlaid web, or bonded carded web, as well as combinations thereof. Suitable polymers can include polypropylene, polyethylene, polyester, and bicomponent materials composed of these polyolefins. Suitable elastomeric materials can include elastic strands, LYCRA elastics, elastic films, cast or blown; nonwoven elastic webs, meltblown or spunbond elastomeric fibrous webs, as well as combinations thereof. Examples of elastomeric materials include KRATON elastomers, HYTREL elastomers, ESTANE elastomeric polyurethanes (available from B.F. Goodrich and Company located in Cleveland, Ohio), or PEBAX elastomers. The topsheet layer may include blends or laminates of fibers, scrim, webs, and films with perforations, apertures, creping, heat activation, embossing, micro-straining, chemically treatment, or the like, as well as combinations thereof.

In desired aspects, the topsheet layer 28 can provide a topsheet elongation-at-peak-load value which is at least a minimum of about 45%, and desirably, is at least about 50%. The topsheet elongation-at-peak-load value can alternatively be at least about 55%, and optionally, can be at least about 75% to provide improved performance. Further configurations of the topsheet layer can provide a topsheet elongation-at-peak-load value of at least about 100% to further improve performance. In other aspects, the topsheet layer 28 can provide a topsheet elongation-at-peak-load value which is not more than a maximum of about 300%. The topsheet elongation-at-peak-load value can alternatively be not more about 250%, and optionally, can be not more than about 200% about to provide desired benefits.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment means may also be employed to suitably interconnect, assemble and/or affix together the various other component parts of the articles which are described herein.

The absorbent body 32 provides an absorbent structure which can include a retention portion 48, such as the shown absorbent pad composed of selected hydrophilic fibers and high-absorbency particles, which holds and stores absorbed liquids and other waste materials. The absorbent body is positioned and sandwiched between the topsheet 28 and backsheet 30 to form the diaper 10. The absorbent body has a construction which is generally compressible, conformable, non-irritating to the wearers skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 900° are designated "nonwettable".

The absorbent body structure 32 can comprise a matrix, such as a matrix of hydrophilic fibers, combined with particles of high-absorbency material, such as superabsorbent polymer material. The absorbent body may, for example, include a matrix web of cellulosic fluff. In particular arrangements, the absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present disclosure. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may include absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the synthetic polymer material.

The high-absorbency or superabsorbent materials can be in many forms such as flakes, powders, particulates, fibers, continuous fibers, networks, solution spun filaments and webs. In the representatively shown arrangement, the high-absorbency material in the absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 100–1200 g/m$^2$. In certain aspects of the invention, the average composite basis weight can be within the range of about 500–1100 g/m$^2$, and alternatively can be within the range of about 600–1000 g/m$^2$ to provide desired performance.

In its various aspects and configurations, the absorbent structure of the invention can exhibit desirable physical properties, such as desired combinations of softness, flexibility and elasticity. Since the absorbent article of the invention can better conform to the body of the wearer, it can reduce gapping at the leg and waist thereby improving the efficiency of the absorbent article to contain and absorb body discharges without leaking. As a result, the absorbent structures and articles of the invention can provide improved fit, reduced leakage, and improved appearance.

As previously described, the absorbent structure of the retention portion 48 can include a selected combination of fibrous material and superabsorbent material. The fibrous material may include absorbent fibers, substantially nonabsorbent fibers, wettable fibers, substantially nonwettable fibers, cellulosic fibers, non-cellulosic fibers, natural fibers, or synthetic fibers, as well as combinations thereof. In particular aspects of the invention the structure of the retention portion 48 can include at least a minimum of about 0.5 wt % superabsorbent material, as determined with respect to the total weight of the dry retention portion. In selected products, such as articles configured for feminine care and light incontinence, the retention portion can alternatively include at least about 0.7 wt % superabsorbent material, and optionally, can include at least about 1 wt % superabsorbent material to provide improved benefits. In other selected products, such as articles configured for infant care diapers and child care training pants, the retention portion can include at least about 15 wt % superabsorbent material, and optionally, can include at least about 30 wt % superabsorbent material to provide improved performance.

In other aspects of the invention, the absorbent structure of the retention portion 48 can include not more than a maximum of about 80 wt % superabsorbent material, as determined with respect to the total weight of the wet-formed material in the dry retention portion 48. In selected products, such as articles configured for feminine care and light incontinence, the retention portion can include not more than about 15 wt % superabsorbent material, and alternatively, can include not more than about 10 wt % superabsorbent material to provide improved benefits. Optionally, the retention portion of such products can include not more than about 5 wt % superabsorbent material to provide desired benefits. In other selected products, such as articles configured for infant care diapers and child care training pants, the retention portion can include not more than about 70 wt % superabsorbent material, and optionally, can include not more than about 60 wt % superabsorbent material to provide improved performance.

With reference to FIG. 3, the retention portion 48 can have a selected incremental absorbent capacity, a selected total absorbent capacity, a selected amount of superabsorbent material, a selected amount of elastomeric fibers, and a selected amount of absorbent fibers.

Particular aspects of the invention can include a retention portion 48 having an incremental absorbent capacity of at least about 5 grams of absorbed liquid per gram of absorbent (5 g/g). The incremental absorbent capacity can alternatively be at least about 8 g/g, and can optionally be at least about 10 g/g to provide improved performance. In addition, the incremental absorbent capacity can be not more than about 50 g/g. Alternatively, the incremental absorbent capacity can be not more than about 40 g/g, and optionally, can be not more than about 35 g/g to provide improved benefits. These values are important because they can provide the product with an advantageous combination of high absorbent capacity and good comfort and fit throughout the product life cycle. Values below the low end of the capacity range can cause the product to leak prematurely due to insufficient capacity. Values greater than the high end of the capacity range can cause the product to sag or gap during use due to an excessive weight of absorbed liquid.

In other aspects of the invention, a total absorbent capacity of the retention portion can be at least a minimum of about 20 grams (20 g) of absorbed liquid, and desirably can be at least at least about 50 g. The total absorbent capacity can alternatively be at least about 100 g, and can optionally be at least about 200 g to provide improved performance. In addition, the total absorbent capacity can be not more than about 1200 g. Alternatively, the total absorbent capacity can be not more than about 800 g, and optionally, can be not more than about 600 g to provide improved benefits.

These values are important because they can provide the product with an desired combination of sufficient absorbent capacity and good comfort and fit throughout the product life cycle. Values below the low end of the capacity range can cause the product to leak prematurely due to insufficient capacity. Values above the high end of the capacity range can cause the product to sag or gap during use due to an excessive weight of absorbed liquid.

The retention portion may include substantially no superabsorbent material. Further aspects of the invention, however, can include a retention portion 48 having superabsorbent material in an amount which is at least about 10 wt %, and alternatively, is at least about 15 wt % to provided improved performance. Additionally, the amount of superabsorbent material can be not more than about 65 wt %, and alternatively, can be not more than about 50 wt % to provide desired benefits. These values are important because they can provide the product article with sufficient capacity at a product thinness level that is desired by consumers. Products with excessively low amounts superabsorbent materials can be more likely to leak prematurely and can be too thick for comfortable wear. Products using larger amounts of superabsorbent materials can look floppy, bunched and wrinkled due to a lack of structural integrity in the retention portion, resulting in poor product appearance, poor fit, poor comfort and poor resistance to leakage.

The superabsorbent material can also be provided at a basis weight which is at least about 5 g/m$^2$, and alternatively, is at least about 10 g/m$^2$ to provide improved performance. In addition, the superabsorbent basis weight can be not more than about 950 g/m$^2$. Alternatively, the incremental absorbent capacity can be not more than about 650 g/m$^2$, and optionally, can be not more than about 400 g/m$^2$ to provide improved benefits. These values are important because they can provide the product with sufficient capacity along with a low product thinness that is desired by consumers. Products with too low an amount of superabsorbent materials can be more likely to leak prematurely and can be too thick to provided desired levels of comfort when wearing the product. Products using greater amounts of superabsorbent materials can look floppy, bunched and wrinkled due to a lack of integrity of the absorbent structure. The low integrity can cause poor appearance, poor fit, poor comfort and excessive leakage.

In still other aspects of the invention, the retention portion can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values are important because they can provide the absorbent retention portion with desired levels of stretchability and structural stability without excessively degrading the physical properties or the liquid-management properties of the absorbent structure. An absorbent retention portion with an excessively low proportion of elastomeric fibers may be insufficiently stretchable, and a retention portion with an excessively high proportion of elastomeric fibers may exhibit an excessive degradation of its absorbency functionalities, such as poor intake, poor distribution, poor retention of liquid and/or an excessive tension force when stretched.

The elastomeric fibers can also be provided at a basis weight which is at least about 1 g/m$^2$. The basis weight can alternatively be at least about 5 g/m$^2$, and can optionally be at least about 10 g/m$^2$ to provide improved performance. In addition, the basis weight can be not more than about 700 g/m$^2$. The basis weight can alternatively be not more than about 500 g/m$^2$, and can optionally be not more than about 300 g/m$^2$ to provide improved benefits. These values are important because they can provide the absorbent retention portion with desired levels of stretchability and structural stability without excessively degrading the physical properties or the liquid-management properties of the absorbent structure. An absorbent retention portion with an excessively low basis weight of elastomeric fibers may be insufficiently stretchable, and a retention portion with an excessively high basis weight of elastomeric fibers may exhibit an excessive degradation of its absorbency functionalities, such as poor intake, poor distribution, poor retention of liquid and/or an excessive resistance to stretching.

The retention portion may include substantially no absorbent fibrous material. In desired aspects of the invention, however, the retention portion can include absorbent fibers in an amount which is at least a minimum of about 10 wt %, and alternatively, is at least about 20 wt % to provided improved performance. Additionally, the amount of absorbent fibers can be not more than about 98 wt %. The amount of absorbent fibers can alternatively be not more than about 90 wt %, and can optionally be not more than about 80 wt % to provide improved benefits. These values are important because they can provide the product with sufficient absorbent capacity while also providing a desired product thinness. Products with an excessively high amount of absorbent fibers can become too thick and feel uncomfortable to the wearer. Products using an excessively low amount of absorbent fibers can look floppy, bunched and wrinkled due to a lack of integrity in the absorbent structure. The low integrity can cause in poor product appearance, poor fit, poor comfort, and excessive leakage.

The absorbent fibers can also be provided at a basis weight which is at least about 10 g/m$^2$, and alternatively is at least about 40 g/m$^2$ to provide improved performance. In addition, the basis weight can be not more than about 1180 g/m$^2$. The basis weight can alternatively be not more than about 900 g/m$^2$, and can optionally be not more than about 640 g/m$^2$ to provide improved benefits. These values are important because they can provide the product with sufficient capacity along with a product thinness that is desired by consumers. Products with an amount of absorbent fibers that is too high can be excessively thick and can feel uncomfortable to the wearer. Products with an amount of absorbent fibers that is too low can look floppy, bunched and wrinkled due to a lack of structural integrity. The low integrity can cause poor product appearance, poor fit, poor comfort and excessive leakage.

With reference to FIG. 3, the retention portion 48 may include an elastomeric coform material. In particular aspects, the elastomeric coform material can have an overall coform basis weight which is at least a minimum of about 50 g/m$^2$. The coform basis weight can alternatively be at least about 100 g/m$^2$, and can optionally be at least about 200 g/m$^2$ to provide improved performance. In addition, the coform basis weight can be not more than about 1200 g/m$^2$. Alternatively, the coform basis weight can be not more than about 900 g/m$^2$, and optionally, can be not more than about 800 g/m$^2$ to provide improved benefits. These values are important because they can provide the absorbent core with desired stretchability and structural stability without excessively degrading the physical properties or the liquid-management functionalities of the retention portion. Retention portions having excessively low proportions of elastomeric coform material may not be sufficiently stretchable. Retention portions having excessively large amounts of elastomeric coform materials can exhibit an excessive degradation of their absorbency functionalities, such as an excessive degradation of intake, distribution and/or retention properties.

Further configurations of the invention can include other materials such as, cellulosic fibers, nonwoven webs, laminates or layers of superabsorbent and non-superabsorbent containing materials, foams, particulates, thermoplastic super absorbent, meltblown particulates, superabsorbent web, waffle, aggregates, modified fiber, synthetic fibers, surfactants, treatments, elastomeric materials, binders, or combinations thereof. Cellulosic fibers may be in the form of modified cellulose, cellulosic and comminuted wood pulp, rayon, cotton, hard and soft woods.

In particular, the retention portion may or may not include a selected amount of an internal or external surface-active agent. Examples of such surface-active agents include TRITON X-102 available from Union Carbide Chemicals and Plastics Company, Inc. located in Danbury, Conn.; LUBRIZOL 85870 available from Lubrizol Corp located in Wickliffe, Ohio; Y12488 produced by OSI Specialties, Inc. located in Tarrytown, N.Y.; AHCOVEL N-62 surfactant from ICI Americas, Inc. located in Wilmington, Del.; and GLUCOPON 220UP surfactant from Henkel Corporation— Emery Group located in Cincinnati, Ohio, as well as combinations thereof.

The surface-active agent can be included in an amount of at least a minimum of about 0.05 wt % of the total weight of the retention portion, and alternatively, can be included in an amount of 0.1 wt % to provide improved performance. Additionally, the amount of surface-active agent can be not more than a maximum of about 3 wt %. The amount of surface-active agent can alternatively be not more than about 2 wt %, and can optionally be not more than about 1 wt % to provide improved benefits. The presence of surface-active agent can advantageously improve the intake performance of the absorbent structure. If the amount of surface-active agent is too high, however, there can be an excessive decrease in the surface tension of the absorbent material, and poor wicking performance.

In desired aspects, the retention portion 48 can have a dry thickness which is at least a minimum of about 0.5 mm, as determined under a restraining pressure of 1.38 KPa. The dry thickness can alternatively be at least about 0.75 mm, and can optionally be at least about 1 mm to provide improved performance. In further aspects, the retention portion 48 can have a dry thickness which is not more than a maximum of about 12 mm. The dry thickness can alternatively be not more than about 10 mm, and can optionally be not more than about 8 mm to provide improved benefits.

In still other aspects, the retention portion 48 can have a dry density which is at least a minimum of about 0.03 g/cm$^3$ as determined under a restraining pressure of 1.38 KPa. The dry density can alternatively be at least about 0.05 g/cm$^3$, and can optionally be within at least about 0.1 g/cm$^3$ to provide improved performance. Additionally, the retention portion 48 can have a dry density which is not more than a maximum of about 0.4 g/cm$^3$.

The dry density can alternatively be not more than about 0.3 g/cm$^3$, and can optionally be not more than about 0.25 g/cm$^3$ to provide improved benefits.

The retention portion 48, in still further aspects, can have a dry tensile strength value which is at least a minimum of about 0.5 Newtons per cm of width (N/cm), as determined by tensioning along the longitudinal direction 26 of the article. The dry tensile strength can alternatively be at least about 1 N/cm, and can optionally be at least about 1.5 N/cm to provide improved performance. Additionally, the retention portion 48 can have a dry tensile strength value which is not more than a maximum of about 4 N/cm, as determined along the longitudinal direction of the article. The dry tensile strength can alternatively be not more than about 3 N/cm, and can optionally be not more than about 2.5 N/cm to provide improved benefits.

Figure 4A:
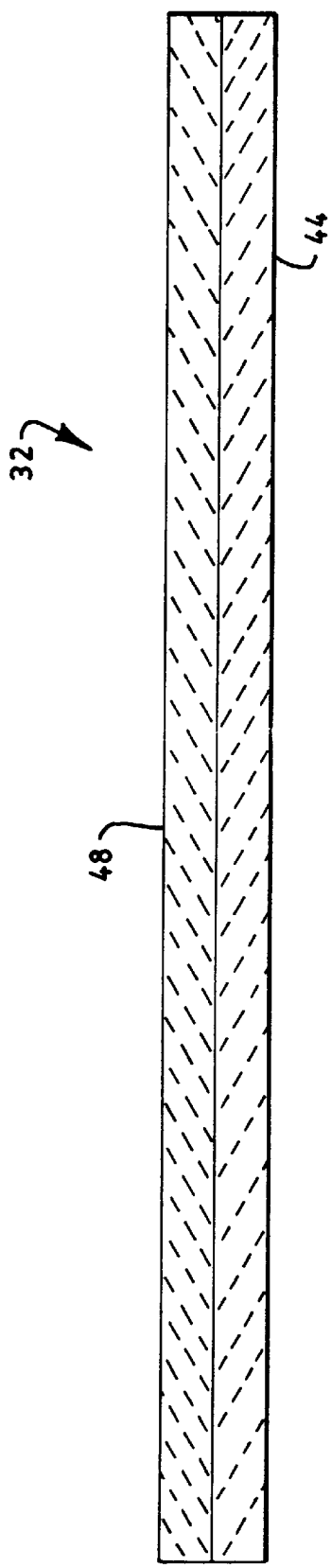
FIG. 4A representatively shows a longitudinal cross-section of the absorbent retention portion representatively shown in FIG. 4.
Figure 5:
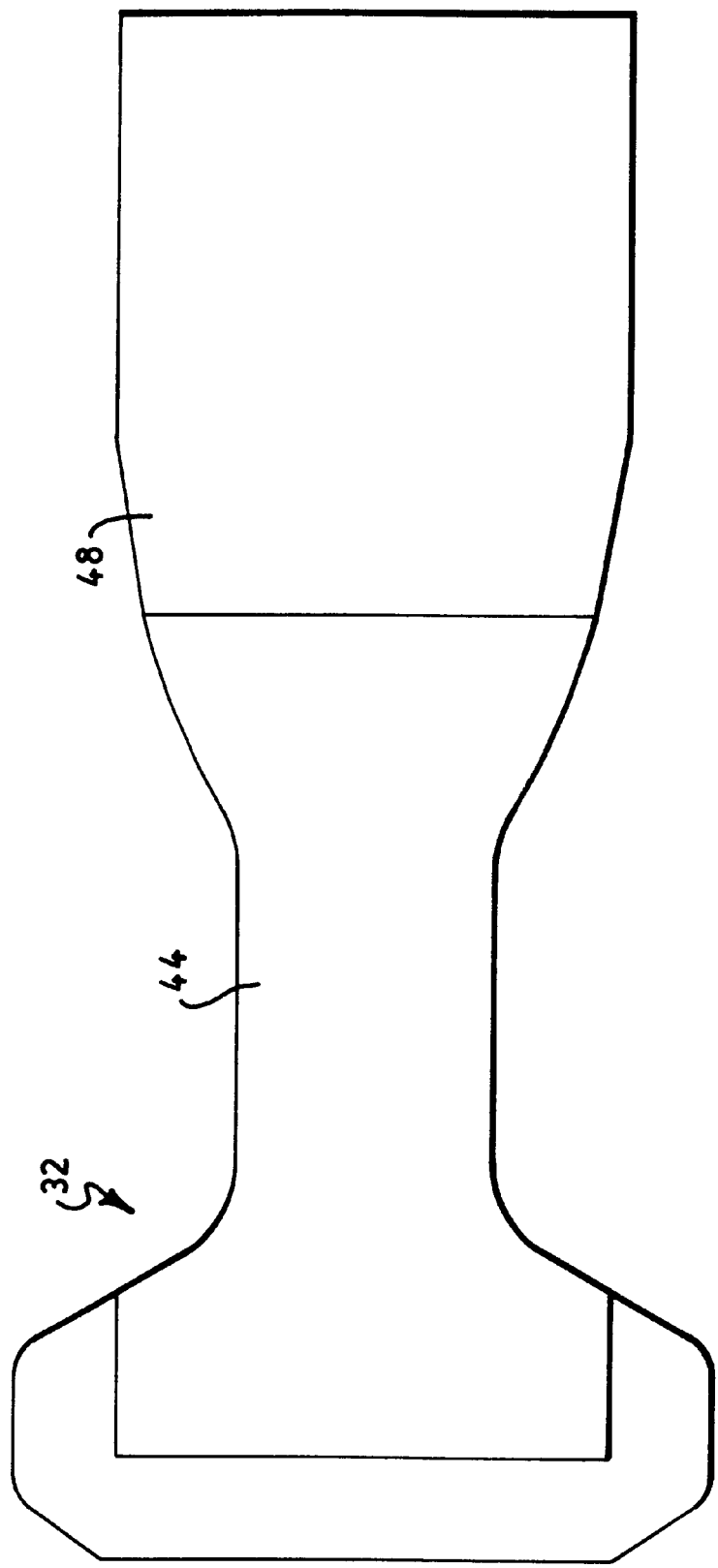
FIG. 5 representatively shows a top, plan view of another absorbent retention portion which can be employed with the present invention, wherein the absorbent retention portion has multiple layers, with a first layer differently shaped and smaller than a second layer.

With reference to FIGS. 4, 4A and 5, the absorbent article may further include a supplemental absorbent layer 44. The supplemental absorbent layer may be positioned on an appointed outward side of the absorbent body structure 32 (e.g. FIGS. 4 and 4A), or may be positioned on an appointed body side of the absorbent body structure (e.g. FIG. 5). The supplemental layer 44 and the retention portion 48 may have substantially the same shape and area-size (e.g. FIG. 4), or may have different shapes and area-sizes (e.g. FIG. 5). Where the supplemental layer provides an intake or distribution layer, the distribution or intake layer can contain a matrix of fibers, such as cellulosic, wood pulp fluff fibers, with substantially no superabsorbent material. Alternatively, the distribution or intake layer can contain at least about 5 wt % of superabsorbent polymer material, as determined with respect to a total weight of the supplemental, distribution or intake layer, and may optionally contain at least about 10 wt % of superabsorbent material to provide improved benefits. Additionally, the amount of superabsorbent material in the distribution or intake layer can be not more than about 50 wt %. The amount of superabsorbent material in the distribution or intake layer can alternatively be not more than about 40 wt %, and optionally can be not more than about 30 wt % to provide improved performance. The distribution or intake layer can also be positioned on a body side or an outward side of the primary retention portion 48, as desired.

Where the supplemental layer 44 provides a supplemental retention layer, the supplemental retention layer can contain a mixture of wood pulp fluff fibers with at least about 5 wt % of superabsorbent material. Alternatively, the supplemental retention layer can contain at least about 10 wt % of superabsorbent polymer material, as determined with respect to a total weight of the supplemental retention layer, and may optionally contain at least about 20 wt % of superabsorbent material to provide improved benefits. Additionally, the amount of superabsorbent material in the supplemental retention layer can be not more than about 80 wt %. The amount of superabsorbent material in the supplemental retention layer can alternatively be not more than about 65 wt %, and optionally can be not more than about 50 wt % to provide improved performance. Also, the supplemental retention layer can be positioned on a body side or an outward side of the primary retention portion 48, as desired.

In desired aspects, the retention portion 48 can be substantially elastomerically stretchable. For example, the retention portion can include elastomeric materials, such as elastomeric polymers, elastomeric urethanes, and natural rubbers. The elastomeric materials can be in form of films, meltblown fibers, spunbond fibers, strands, webs, continuous fibers or fibers. Examples of elastomeric materials can include KRATON, HYTREL, ESTANE, LYCRA or PEBAX elastomers. The absorbent material can be made in an airlaid process, spunbond process, air-formed process, carding process, foam process, wet laid process, or meltblown process, as well as combinations thereof. Additional processes that may improve the form and elasticity of the absorbent materials can include creping, heat treating, chemically treating, aperturing, embossing, micro-straining, and corrugating the absorbent, as well as combinations thereof.

Suitable absorbent structures and retention portions are described in U.S. patent application Ser. No. 09/197,268 entitled ELASTIC ABSORBENT STRUCTURES by Debra Jean McDowall et al. filed Nov. 20, 1998. The entire disclosure of this document is incorporated herein by reference in a manner that is consistent herewith.

In particular aspects of the invention, the retention portion 48 can have a retention portion elongation-at-peak-load value which is at least a minimum of about 10%. Alternatively, the retention portion elongation-at-peak-load value can be at least about 30%, and optionally, can be at least about 40% to provide improve performance. In other aspects, the retention portion elongation-at-peak-load value can be up to a maximum of about 500%, or more. The retention portion elongation-at-peak-load value can alternatively be up to about 300%, and optionally, can be up to about 200%, or more, to provide improved benefits.

Further aspects of the invention can include a retention portion 48 having an elongation-at-break-load value (elongation-at-break value) which is at least a minimum of about 50%. The retention portion can alternatively have an elongation-at-break value which is at least about 75%, and optionally is at least about 100% to provide improved performance. In additional aspects, the retention portion 48 can have an elongation-at-break-load value which is not more than a maximum of about 500%. The retention portion can alternatively have an elongation-at-break value which is not more than about 300%, and optionally is not more than about 200% to provide improved benefits.

In typical, non-stabilized absorbent structures, the percent elongation-at-peak-load value approximately equals the elongation-at-break value. After the typical, non-stabilized absorbent structures have been subjected to their elongation-at-peak-load value, the absorbent structures can exhibit undesired bunching, separation, or poor integrity and can provide inadequate absorbent performance.

In the elastomeric retention portion employed in the present invention, however, both the elongation-at-peak-load value and the elongation-at-break value are important, and the two values can be different. The elastomeric retention portion can be in an operative condition after it has been subjected to its peak-load force, and can remain in an operative condition until it has been subjected to its break-load force. As a result, the elastomeric retention portion employed in the present invention can exhibit reduced bunching, reduced separation, and improved integrity following the elongation generated at the peak load.

The article of the invention can also include a distinctive combination of tensile strength and elongation properties. In particular aspects, the article can provide an overall, composite-article tensile load force value which is at least a minimum of about 250 grams per inch (about 0.97 N/cm), as determined at a composite-article elongation of 45%. The article load value can alternatively be at least about 300 g/inch (about 1.16 N/cm), and optionally, can be at least about 350 g/inch (about 1.35 N/cm) to provide improved performance. In other aspects, the article can provide an article tensile load value which is not more than a maximum of about 750 g/inch (about 2.9 N/cm), as determined at the article elongation of 45%. The article load value can alternatively be not more than about 600 g/inch (about 2.9 N/cm), and optionally, can be not more than about 450 g/inch (about 2.9 N/cm) to provide improved benefits.

The article of the invention can also provide a composite-article elongation value which is at least a minimum of about 4% when subjected to a tensile force of 100 g/inch (0.386 N/cm). Alternatively, the article elongation value can be at least about 5%, and optionally, can be at least about 7% to provide improve performance. In other aspects, the article elongation value can be up to a maximum of about 50%, or more. The article elongation value can alternatively be up to about 25%, and optionally, can be up to about 15%, to provide desired performance.

In other aspects, the article can provide a composite-article elongation-at-peak-load value which is at least a minimum of about 45%, and desirably, is at least about 50%. The article elongation-at-peak-load value can alternatively be at least about 60%, and can optionally be at least about 70% to provide improved performance. In addition, the article elongation-at-peak-load value can be not more than about 500%. Alternatively, the article elongation-at-peak-load value can be not more than about 350%, and optionally, can be not more than about 200% to provide improved benefits.

A product having the advantageous elongation-at-peak-load value does not suffer from the many deficiencies associated with non-stretch products, but instead provides the distinctive benefits to the wearer. Products with less than the desired elongation-at-peak-load values do not provide a clearly recognizable level of these benefits to the wearer. Such benefits can, for example, include a flexible body-conforming fit that provides a trim and appealing underwear-like appearance. The improved article can also provide reduced gapping and can increase the efficiency of the product with regard to containing and absorbing urine and feces with reduced leakage. The article can better survive wear-related stresses, can reduce product deformation, bunching, and breaking apart during use, and can provide superior comfort. Additionally, the article can provide a self-adjusting fit which can maintain a desired position and body coverage regardless of the wearer's position and activity. The article can also be easier to apply due to its ability to conform to the wearer's body while product is worn. The article can fit a broader size range, and can provide less binding or restriction. Instead, the article can more readily move with the wearer, and allow a more natural and free level of mobility.

In desired aspects, a quotient of an elongation value of the backsheet member 30 divided by the elongation value of the composite article can be at least minimum of about 1.1, where each elongation value is determined at a tensile loading of 100 grams per inch (0.386 N/cm). To determine the quotient, the elongation value of each stated component is measured separately. Each stated component is separately subjected to the described tensile loading to determine the elongation value for the individual component. After independently measuring the individual elongation values, the quotient can be calculated. The quotient can alternatively be at least about 1.2, and can optionally be at least about 1.3 to provide improved performance. In addition, the quotient can be not more than about 20. Alternatively, the incremental absorbent capacity can be not more than about 10, and optionally, can be not more than about 2 to provide improved benefits.

The quotient of the backsheet member elongation to the total product elongation within the selected values can be advantageous, since an article with a quotient that is too low does not provide sufficient stretch of the backsheet member to allow the article to maintain a trim appearance, good body conformance/coverage, and resist gapping as the product undergoes wear. Also, a product with excessively low quotient values does not allow sufficient stretch of the backsheet member to accommodate the space required in the product to accept bowel movements and to accommodate the swelling of the absorbent that occurs as a result of multiple voidings of urine. Products having excessively high quotients can exhibit over-conformance, excessive wrinkling of the backsheet member, excessive body folding/creasing and excessive loss of the highly desirable smooth appearance along the outside surface of the backsheet member. Products with quotient values that are too high can cause the other components of the product to fold and buckle, and can degrade the wearer's comfort. Also, products with excessively high quotient values can exhibit an excessive pulling by the backsheet member, which can result in excessive gapping in the waist regions, excessive bunching in the crotch region, poor fit and poor absorbent efficiency.

In other aspects, a quotient of an elongation value of the retention portion 48 divided by the elongation value of the composite article can be at least a minimum of about 1.01, where each elongation value is determined at a tensile loading of 100 grams per inch (0.386 N/cm). To determine the quotient, the elongation value of each stated component is measured separately. Each stated component is separately subjected to the described tensile loading to determine the elongation value for the individual component. After independently measuring the individual elongation values, the quotient can be calculated. The quotient can alternatively be at least about 1.1, and can optionally be at least about 1.2 to provide improved performance. Additionally, the incremental absorbent capacity can be not more than a maximum of about 5. Alternatively, the incremental absorbent capacity can be not more than about 3, and optionally, can be not more than about 2 to provide improved benefits.

When the quotient of the elongation of the retention portion divided by the elongation of the total product is too low, the absorbent can excessively restrict the stretch properties and associated benefits of the product, particularly in the arrangement where the retention portion has greater strength than the other components of the product. When the strength of the absorbent retention portion is less than the other components and the quotient is too low, the absorbent can exhibit an excessive amount of breakage and clumping during use, and can exhibit poor absorbency and uncomfortable fit.

Products having excessively high quotient values of the elongation of the retention portion divided by the elongation of the total product can exhibit excessive deformation, buckling, and wrinkling of the absorbent within the product. The products can also exhibit an undesired loss of trim fit and smooth appearance, as well as excessive gapping and reduced efficiency of the absorbent. Additionally, products with excessively high quotient values can incorporate excessive amounts of elastic components into the absorbent, which raises raw material and manufacturing expenses without providing a cost effective benefit.

In further aspects, a quotient of an elongation value of the retention portion 46 divided by an elongation value of the backsheet member 30 can be at least about 0.06, where each elongation value is determined at a tensile loading of 100 grams per inch (0.386 N/cm). To determine the quotient, the elongation value of each stated component is measured separately. Each stated component is separately subjected to the described tensile loading to determine the elongation value for the individual component. After independently measuring the individual elongation values, the quotient can be calculated. The quotient of the elongation of the retention portion divided by the elongation of the backsheet member can alternatively be at least about 0.1, and can optionally be at least about 0.2 to provide improved performance. In addition, the quotient can be not more than a maximum of about 0.95. Alternatively, the incremental absorbent capacity can be not more than about 0.75, and optionally, can be not more than about 0.5 to provide improved benefits.

If the quotient of the absorbent elongation divided by the backsheet member elongation is too low, the article does not allow the absorbent retention portion to stretch enough, and the insufficient stretch can cause the backsheet member to be excessively constrained by the retention, resulting in poor fit and performance. If the quotient values are too high, the article may not sufficiently maintain the desired shape of the retention portion, but instead, can allow the retention portion to excessively mold to the body contours, causing a wrinkled/bunched backsheet member which is highly undesirable for good fit, comfort, and appearance.

In additional aspects, a quotient of a tensile force value in the backsheet member 30 as determined at a 15% backsheet elongation, divided by a tensile force value in the composite-article, as determined at a 15% composite-article elongation, can be at least a minimum of about 0.05. To determine the quotient, the tensile force value of each stated component is measured separately. Each stated component is separately subjected to its described elongation to determine the resulting tensile force value for the individual component. After independently measuring the individual tensile force values, the quotient can be calculated. The quotient of the tensile force in the backsheet member, divided by the tensile force in the article can alternatively be at least about 0.07, and can optionally be at least about 0.1 to provide improved performance. In addition, the quotient of the tensile force in the backsheet member, divided by the tensile force in the article can be not more than about 0.9. Alternatively, the quotient can be not more than about 0.6, and optionally, can be not more than a maximum of about 0.3 to provide improved benefits.

The quotient of the tensile force in the backsheet member divided by that of the total product is too low, the backsheet member may not provide sufficient strength to resist in-use product deformation and breakage forces, resulting in poor product fit and functionality. If the quotient value is too high, the force required to elongate the backsheet member relative to the total product can become excessive, causing reduced product conformance, poor fit, and gapping induced absorbent inefficiency.

In still other aspects, a quotient of a tensile force in the retention portion 48, as determined at a 15% retention portion elongation, divided by a tensile force in the composite-article, as determined at a 15% composite-article elongation, can be at least a minimum of about 0.1. To determine the quotient, the tensile force value of each stated component is measured separately. Each stated component is separately subjected to its described elongation to determine the resulting tensile force value for the individual component. After independently measuring the individual tensile force values, the quotient can be calculated. The quotient can alternatively be at least about 0.5, and can optionally be at least about 0.6 to provide improved performance. In addition, the quotient of the tensile force in the retention portion, divided by the tensile force in the article can be not more than a maximum of about 0.99. Alternatively, the quotient can be not more than about 0.8, and optionally, can be not more than about 0.7 to provide improved benefits.

If the quotient of the tensile force in the retention portion, divided by the tensile force in the composite article is too low, the article may not have enough strength to prevent excessive deformation and breaking during product use, leading to poor fit and absorbent efficiency. If the quotient value is too high, the load required to stretch the absorbent becomes excessively higher than the loads needed to stretch the other product components. As a result, the absorbent may not stretch in concert with the other diaper components but may instead degrade overall product conformance, coverage, and absorbent efficiency. If the applied force is sufficient to elongate the other product components, but not sufficient to elongate the absorbent retention portion, then the other product components can separate away from the retention portion, leading to excessive product deformation and poor fit.

In still further aspects, a tensile force in the retention portion 48, as determined at a 15% retention portion elongation divided by a tensile force in the backsheet member 30, as determined at a 15% backsheet elongation, can be at least a minimum of about 1.5. To determine the quotient, the tensile force value of each stated component is measured separately. Each stated component is separately subjected to its described elongation to determine the resulting tensile force value for the individual component. After independently measuring the individual tensile force values, the quotient can be calculated. The tensile force in the retention portion, divided by the tensile force in the backsheet member can alternatively be at least about 2.5, and can optionally be at least about 5 to provide improved performance. In addition, the quotient of the tensile force in the retention portion, divided by the tensile force in the backsheet member can be not more than about 8. Alternatively, the quotient can be not more than about 7, and optionally, can be not more than about 6 to provide improved benefits.

If the quotient of the tensile force in the retention portion, divided by the tensile force in the backsheet member is too low, the absorbent may not provide sufficient strength to resist in-use backsheet member deformation and breakage forces, resulting in poor product fit and functionality. If the quotient value is too high, the force required to elongate the absorbent retention portion relative to the backsheet member can become excessive, and can cause a reduced product conformance, poor fit, gapping and excessive leakage.

The physical properties, such as tensile strength, tensile load and elongation, of a material or component can be determined by conventional techniques that are well known in the art. A suitable technique can incorporate ASTM procedure D 3039 "Tensile Properties of Polymer Matrix Composite Materials", as described below in the Tensile Testing section of the Procedures portion of the present disclosure.

To improve the containment of the high-absorbency material, absorbent body structure 32 may include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 which corresponds to U.S. Pat. No. 5,490,846. Other suitable surge management materials are described in U.S. patent application Ser. No. 754,417 filed Nov. 22, 1996 and entitled HETEROGENEOUS SURGE MATERIAL FOR ABSORBENT ARTICLES by R. Dodge et al. which corresponds to U.S. Pat. No. 5,820,973 issued Oct. 13, 1998. The entire disclosures of these documents are hereby incorporated by reference in a manner that is consistent herewith.

The article of the invention may or may not include leg elastic members 34. Where the leg elastic members are included, the leg elastic members 34 can be located in the lateral side margins of the article. In the shown diaper 10, for example, the leg elastic members are assembled into the lateral side margins 20, and are arranged to draw and hold the diaper against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like.

For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet member 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet member and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT, which corresponds to U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995, the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet member 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical fastening element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include a loop type of mechanical fastening element; and the complementary, second fastening component, which is operatively joined and attached to the appointed landing zone member, can include a hook type of fastening element.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

Each fastener tab 36 can have a variety of rectilinear or curvilinear shapes and planforms, as well as combinations thereof. For example, as illustrated in the representatively shown arrangements, the fastener tab can have a contoured, bell-shape. Alternatively, the fastener tab can have a quadrilateral, generally rectangular shape. In addition, the longitudinally extending, laterally outward, terminal edge of the fastener tab may be substantially straight. Optionally, the longitudinally extending, laterally outward, terminal edge of the fastener tab may have only a limited amount of waviness.

In the various configurations of the invention, the desired first fastener component can be a hook material which provides hook-type engagement members. An example of a suitable hook material is a micro-hook material which is distributed under the designation VELCRO HTH 829, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units). Other suitable hook materials can include VELCRO HTH 858, VELCRO HTH 851 and VELCRO HTH 863 hook materials.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present disclosure, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996; the entire disclosure of which is incorporated herein by reference in a manner that is consistent herewith.

In the various configurations of the invention, the loop material need not be limited to a discrete or isolated patch on the outward surface of the article. Instead, the loop material can, for example, be provided by a substantially continuous, outer fibrous layer which is integrated to extend over substantially the total exposed surface area of a cloth-like outer cover employed with the desired article.

In the various arrangements of the invention, the engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch of the "width" of engagement between the first and second fastener components. In further arrangements, the fastening engagement may provide a peel force value of not less than about 100 gmf/inch to provide improved advantages. In desired configurations, the fastening engagement may provide a peel force value of not less than about 200 gmf per inch of the "width" of engagement between the first and second fastener components. Alternatively, the peel force is not less than about 300 gmf/inch, and optionally is not less than about 400 gmf/inch to further provide improved benefits. In other aspects, the peel force is not more than about 1,200 gmf/inch. Alternatively, the peel force is not more than about 800 gmf/inch, and optionally is not more than about 600 gmf/inch to provide improved performance.

The engagement force between the selected first fastener component and its appointed and cooperating second fastener component may additionally provide a shear force value of not less than about 400 gmf per square inch of the area of engagement between the first and second fastener components. Alternatively, the shear force is not less than about 1,000 gmf/in$^2$, and optionally, is not less than about 1,700 gmf/in$^2$. In further aspects, the shear force can be up to about 4,400 gmf/in$^2$, or more. Alternatively, the shear force is not more than about 3,900 gmf/in$^2$, and optionally is not more than about 3,500 gmf/in$^2$ to provide improved performance.

Desirably, the securing engagement between the first and second fastener components should be sufficient to prevent a disengagement of the fastener tab 36 away from the landing member 50 when the fastener tab 36 is subject to a tensile force of at least about 3,000 grams when the tensile force is applied outwardly along the lateral direction, aligned generally parallel with the plane of the backsheet member 30 of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Procedures

Tensile Testing

For the purposes of the present invention, the properties, such as tensile strength, tensile load and elongation, of a material or component can be determined by ASTM Procedure D 3039 "Tensile Properties of polymer Matrix Composite Materials", with the following specifications and particulars:

Specimen length (aligned parallel to the applied force): 180 mm;

Gauge length: 130 mm;

Specimen width (aligned perpendicular to the applied force): 1 inch (25.4 mm);

Jaw width (measured parallel to the applied force): ½ inch (12.7 mm);

Jaw length (measured perpendicular to the applied force): 4 inches (101.6 mm);

Jaw speed: 500 mm/min.

A suitable testing device is a SINTECH tensile tester (available from Sintech, Inc., a business having offices located in Research Triangle Park, N.C.), or an equivalent device. The tensile tester is operatively programmed with suitable software, such as TESTWORKS software (available from MTS Systems Corporation, a business having offices located in Edens Prairie, Minn.), or an equivalent software.

Composite, multi-component specimens, such as specimens of a composite-article or a composite retention portion, were stapled at their length-wise ends at locations outside of the test area to prevent slippage of the individual materials within the composite when the composite is mounted in the jaws of the testing device.

Figure 6:
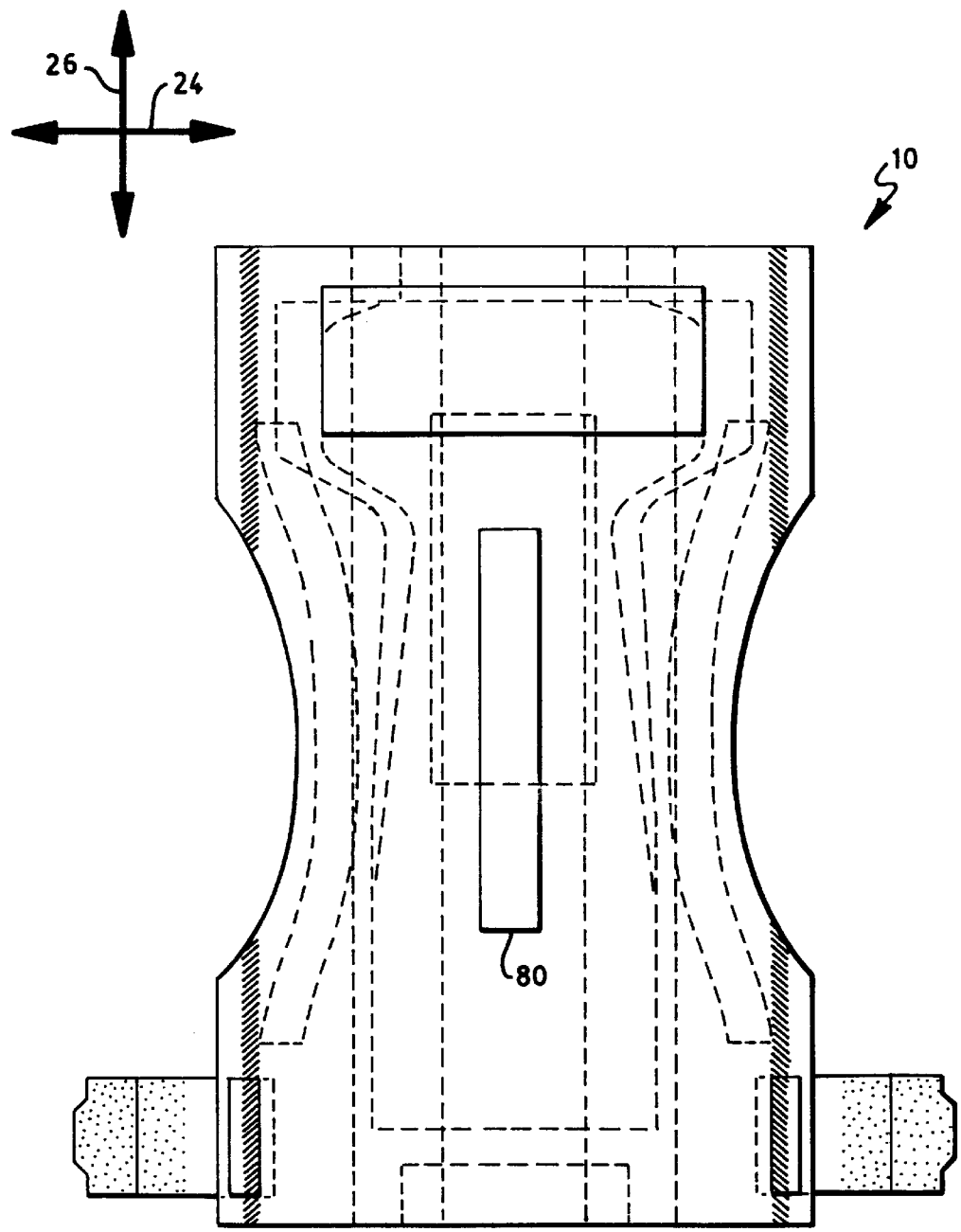
FIG. 6 representatively shows the location and orientation of a test specimen taken from a product article.

The 1-inch (25.4 mm) width of each specimen can be cut with a JDC-1-10 precision cutter (available from Thwing-Albert Instrument Company, a business having offices located in Philadelphia, Pa.), or an equivalent device.

Where a test specimen 80 (single component specimen, or multi-component specimen) is removed from an individual product article, each test specimen is desirably removed from the product article at a location which was centered along both the longitudinal dimension and lateral dimension of the article, as representatively shown in FIG. 6. The location is selected to avoid the effects of conventional elasticized components that may be present; such as elasticized leg bands, elasticized waistbands, elasticized containment flaps and the like.

Three specimens are tested per sample. The reported value of the particular property being determined for each sample is the arithmetic average of the corresponding data points measured for the three specimens during the testing. All specimens are pulled until the specimen breaks or until the testing apparatus reaches its upper stopper height, which is set at 97 cm.

The following data points were recorded for each test specimen:

Break load (g/in);

Elongation-at-break-load (%);

Peak load (g/in);

Elongation-at-peak-load (%);

Elongation at 100 g load (%);

Load at 15% elongation (g/in or N/cm);

Load at 45% elongation (g/in or N/cm);

The peak load is typically determined at the highest-occurring yield point. For this test a yield point is the occurrence of an increase in strain without an increase in stress (zero slope). If, however, when the testing apparatus reaches the 97 cm stopper height, the test sample is supporting a tensile load that is greater than the load at the highest-occurring yield point, then the peak load is the load recorded when the apparatus reaches the 97 cm stopper height.

The break-load is the load applied to the specimen at the breaking point of the specimen. The breaking point is the point during tensile testing at which the load force supported by the specimen exhibits a 60% decrease, as determined by the instantaneous change in load at incremental changes in elongation. At that point the test is ended.

The percent elongation can be determined in accordance with the following formula:

$$\% \text{ elongation} = (L_f - L_0) * 100 / L_0;$$

where:

$L_0$=initial, non-elongated length $L_f$=final, elongated length.

Modified Hydrohead For Stretched Materials Testing

To prepare a sample specimen for hydrohead testing, cut the sample to the form of a 6.5 inch×6.5 inch (16.5 cm×16.5 cm) square.

Place the specimen in the SINTECH tester, and center the specimen in the jaws. The jaws are 10 inches (25.4 cm) long (as measured in the direction perpendicular to applied force), and 1 inch (2.54 cm) wide (as measured in the direction parallel to applied force). The gauge length is set to 130 mm (5.1 in), and the jaw speed is set to 500 mm/min. Pull each specimen to the desired elongation. If the sample tears or if visible holes form, the test is ended, and the specimen is considered to be capable of supporting a "zero" hydrohead of water.

Figure 7:
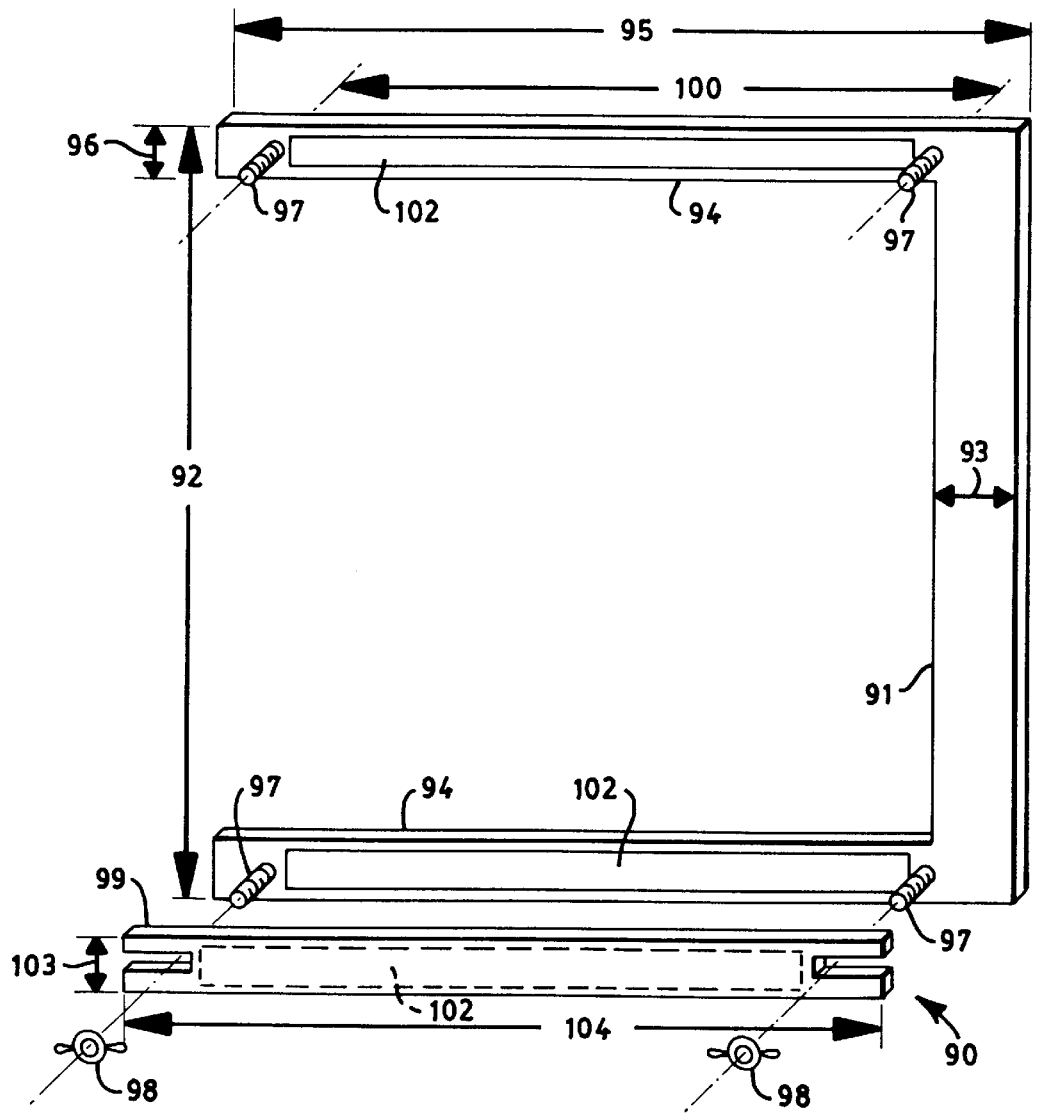
FIG. 7 shows a representative clamping frame employed to hold a test a specimen in a stretched, elongated condition.

If the specimen does not tear and does not form visible holes, clamp the two, opposed, tensioned ends of the stretched specimen in a clamping frame to hold the specimen in its stretched, elongated condition. A suitable clamping frame 90 is representatively shown in FIG. 7.

The illustrated clamping frame 90 is a three-sided structure which is rectangular in form. The frame can be constructed from any material that is sufficiently strong and rigid to hold the specimen in its appointed stretched and elongated condition. For example, the frame can be constructed from 0.5 inch (1.27 cm) thick LEXAN sheet polymer material (available from General Electric Company, a business having offices located in Pittsfield, Mass.). The frame has a base 91 with a base length 92 measuring 7 inch (17.8 cm) and a base width 93 measuring 0.75 inch (1.9 cm). A frame arm 94 is affixed to extend from each end of the frame base. Each arm 94 has an arm length 95 and an arm width 96 which are sufficient to accommodate the desired clamping mechanism and the stretched specimen. In the shown configuration, for example, the arm length can be 7.25 inch (18.4 cm) and the arm width can be 0.5 inch (1.27 cm). A layer of slip-resistant material 102 is desirably affixed to an appointed mounting surface of each arm 94. The slip-resistant material can, for example, be a 1/16 inch (1.6 mm) thick, GARLOCK 22 red rubber gasket material, 80 durometer (available from Garlock, a business having offices located in Dayton, Ohio). In the shown arrangement, the clamping mechanism includes a pair of threaded studs 97 is affixed to each clamping arm 94 with a stud spacing 100 that is sufficiently large to allow the placement of the stretched specimen between the two studs on each arm. The shown clamping frame, for example, can have a stud spacing which measures 6 inch (15.2 cm) along the length of each frame arm. A pair of clamping bars 99 are constructed of a material that is sufficiently rigid and strong to hold and maintain the stretched specimen in the frame 90. In the shown configuration, for example, each clamping bar can be constructed of 0.5 inch (1.27 cm) thick LEXAN sheet material. Each clamping bar is of sufficient size to incorporate a pair of apertures, such as holes or slots, which are suitably sized and spaced-apart to accommodate the placement of a corresponding pair of the threaded studs 97 therethrough. In the shown arrangement, each clamping bar has a bar width 103 of 0.5 inch (1.27 cm) and a bar length 104 of 7 inch (17.8 cm). A layer of the slip-resistant material 102 is desirably affixed to an appointed clamping surface of the clamping bar. A first clamping bar is placed to hold the first tensioned end of the specimen, and a second clamping bar (not shown) is placed to hold the opposite, second tensioned end of the specimen. Threaded fasteners, such as the shown wing nuts 98, are screwed onto their corresponding threaded studs 97 and tightened to hold and maintain the specimen in the desired stretched condition.

After the tensioned ends of the specimen have been affixed to the clamping frame, remove the specimen from the jaws of the tensile tester. Keeping the specimen secured at the desired elongation, place the specimen in the hydrostatic pressure tester.

Test the hydrostatic pressure resistance of the specimen in accordance with Federal Test method Standard number 191A Method 5514, 1978. A suitable test apparatus is a TEXTEST FX3000 hydrostatic head tester (available from Schmid Corporation located in Spartanburg, S.C. 29301). A small test head with an area of 25.7 cm² is used, and the test head can be part number FX3000-26. The specimen tested should be free of tears, holes, folds, wrinkles, or any distortions that would make the specimens abnormal from the rest of the test materials. For the testing, employ water which has been processed through distillation, reverse osmosis, or de-ionization. The water is provided at a temperature of 75°±10° F. (24±6° C.), and is introduced at a rate of 61.2 cm/min.

Three specimens of each sample material are tested. The reported value of the particular property being determined for each sample is the arithmetic average of the corresponding data points measured for the three specimens during the testing. The recorded data includes the individual hydrostatic head, test measurements, in centimeters of water. The average values and the standard deviations of the tested specimens can then be calculated.

The following Examples are presented to provide a more detailed understanding of the invention, and are not intended to limit the scope of the invention.

EXAMPLE 1

In Sample 1, the topsheet layer was a nonwoven, spunbond polypropylene fabric composed of about 2 to 3 denier fibers formed into a web which had a basis weight of about 12 g/m² and was necked approximately 60% (available from Kimberly-Clark Corporation, a business having offices located in Dallas, Tex.). About 9 g/m² of strand material composed of KRATON G2760 elastomer (available from Shell Chemical Company located in Houston, Tex.) were adhered to the necked spunbond material and distributed with about eight strands per inch (2.54 cm). The fabric was surface treated with AHCOVEL surfactant (available from ICI Americas, Inc.—Emery Group of Wilmington, Del.) at a 0.6 weight percent (wt %) add-on level. The absorbent (retention portion) was an approximately 455 g/m² composite which included about 259 g/m² of SAICCOR 94 eucalyptus pulp (available from Central National-Gottesman, Inc. located in Purchase, N.Y.); 173 g/m² of FAVOR SXM 880 superabsorbent particles (available from Stockhausen Inc. located in Greensboro, S.C.); and 23 g/m² of KRATON G2740, styrene-butadiene block copolymer elastomeric resin (available from Shell Chemical Company located in Houston, Tex.). The absorbent was surface treated with a 3% solution of a 3:1 ratio (by active weight) of AHCOVEL base N62 surfactant (available from ICI Americas, Inc. of Wilmington, Del.) and GLUCOPON 220UP surfactant (available from Henkel Corporation—Emery Group located in Cincinnati, Ohio). The outer cover (backsheet member) was a stretch thermal laminate composed of a 17 g/m² polypropylene spunbond fabric bonded to a 17.7 g/m² co-extruded linear-low-density-polyethylene film having a 2.5% by basis weight skin layer of catalloy and ethyl vinyl acetate (available from Kimberly-Clark Corporation a business having offices located in Dallas, Tex.).

EXAMPLE 2

In Sample 2, the topsheet layer was a nonwoven, spunbond polypropylene fabric composed of about 2 to 3 denier fibers formed into a web which had a basis weight of about 12 g/m² and was necked approximately 60%. About 9 g/m² of strand material composed of KRATON G2760 elastomer were adhered to the necked spunbond material and distributed with eight strands per inch (2.54 cm). The fabric was surface treated with AHCOVEL surfactant at a 0.6 wt % add-on level. The absorbent, retention portion was an approximately 330 g/m² composite which included about 126 g/m² of softwood pulp with 16% hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was a stretch thermal laminate composed of a 17 g/m² polypropylene spunbond fabric bonded to a 17.7 g/m² co-extruded linear-low-density-polyethylene film having a 2.5% by basis weight skin layer of catalloy and ethyl vinyl acetate (available from Kimberly-Clark Corporation located in Dallas, Tex.).

EXAMPLE 3

In Sample 3, the topsheet layer was a nonwoven, spunbond polypropylene fabric composed of about 2 to 3 denier fibers formed into a web which had a basis weight of about 12 g/m² and was necked approximately 60%. About 9 g/m² of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion included two layers. Each layer was an approximately 330 g/m² composite composed of about 126 g/m² softwood pulp with 16 wt % hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was a stretch thermal laminate composed of a 17 g/m² polypropylene spunbond fabric and a 17.7 g/m², co-extruded linear-low-density-polyethylene film having a 2.5% by basis weight skin layer of catalloy and ethyl vinyl acetate (available from Kimberly-Clark Corporation located in Dallas, Tex.).

EXAMPLE 4

In Sample 4, the topsheet layer was a nonwoven, spunbond polypropylene fabric composed of about 2 to 3 denier fibers formed into a web which had a basis weight of about 12 g/m² and was necked approximately 60%. About 9 g/m² of strand material composed of KRATON G2760 elastomer were adhered to the necked spunbond material and distributed with about eight strands per inch (2.54 cm). The fabric was surface treated with AHCOVEL surfactant at 0.6 wt % add-on level. The absorbent, retention portion was an approximately 330 g/m², air formed composite composed of 37 wt % FAVOR SXM 880 superabsorbent particles (available from Stockhausen Inc. located in Greensboro, S.C.), and 63 wt % softwood pulp with 16 wt % hardwood (available from U.S. Alliance Forest Products located in Coosa River, Ala. under the designation CR 1654). The air formed composite was formed onto a 17 g/m² cellulosic wetlaid tissue, and this tissue was included as part of the absorbent retention portion during testing. The outer cover, backsheet member included 14 g/m² of KRATON G2760, elastomeric resin strands (available from Shell Chemical Company) laminated with 0.3 g/m² of H2525A adhesive (available from AtoFindley Adhesive located in Milwaukee, Wis.), between two facings, each facing composed of a 24 g/m², point bonded bicomponent spunbond fabric. The strands were distributed with about 12 strands per inch (2.54 cm) of sample width.

EXAMPLE 5

In Sample 5, the topsheet layer was a nonwoven, spunbond polypropylene fabric composed of about 2 to 3 denier fibers formed into a web which had a basis weight of about 12 g/m² and was necked approximately 60%. About 9 g/m² of strand material composed of KRATON G2760 elastomer were adhered to the necked spunbond material and distributed with about eight strands per inch (2.54 cm). The fabric was surface treated with AHCOVEL surfactant at 0.6 wt % add-on level. The absorbent, retention portion was an approximately 330 g/m², air formed composite composed of 37% FAVOR SXM 880 superabsorbent particles (available from Stockhausen Inc. located in Greensboro, S.C.), and 63% softwood pulp with 16% hardwood (available from U.S. Alliance Forest Products located in Coosa River, Ala. under the designation CR 1654). The air formed composite was formed onto a 17 g/m² cellulosic wetlaid tissue. This tissue was included as part of the absorbent retention portion during testing. The outer cover, backsheet member was a stretch thermal laminate composed of a 17 g/m² polypropylene spunbond fabric bonded to a 17.7 g/m², co-extruded linear-low-density-polyethylene film having a 2.5% by basis weight skin layer of catalloy and ethyl vinyl acetate (available from Kimberly-Clark Corporation located in Dallas, Tex.).

EXAMPLE 6

In Sample 6, the topsheet layer was a 17 g/m² polypropylene spunbond nonwoven fabric treated for wettability with AHCOVEL N-62 surfactant. The spunbond material is available from Kimberly-Clark located in Dallas, Tex. The absorbent, retention portion was an approximately 455 g/m² composite composed of about 259 g/m² of SAICCOR 94 eucalyptus pulp (available from Central National-Gottesman, Inc. located in Purchase, N.Y.); 173 g/m² of FAVOR SXM 880 superabsorbent particles (available from Stockhausen Inc. located in Greensboro, S.C.); and 23 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was a stretch thermal laminate composed of a 17 g/m² polypropylene spunbond fabric bonded to a 17.7 g/m² co-extruded linear-low-density-polyethylene film having a 2.5% by basis weight skin layer of catalloy and ethyl vinyl acetate (available from Kimberly-Clark Corporation located in Dallas, Tex.).

EXAMPLE 7

In Sample 7, the top sheet was a 17 g/m² polypropylene spunbond nonwoven fabric treated for wettability with AHCOVEL N-62 surfactant. The spunbond material is available from Kimberly-Clark located in Dallas, Tex. The absorbent, retention portion was an approximately 330 g/m² composite composed of about 126 g/m² of softwood pulp with 16% hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was a stretch thermal laminate composed of a 17 g/m² polypropylene spunbond fabric bonded to a 17.7 g/m² co-extruded linear-low-density-polyethylene film having a 2.5% by basis weight skin layer of catalloy and ethyl vinyl acetate (available from Kimberly-Clark Corporation located in Dallas, Tex.).

EXAMPLE 8

In Sample 8, the topsheet layer was a 17 g/m² polypropylene spunbond nonwoven fabric treated for wettability with AHCOVEL N-62 surfactant. This spunbond material is available from Kimberly-Clark located in Dallas, Tex. The absorbent, retention portion included two layers. Each layer was an approximately 330 g/m² composite composed of about 126 g/m² softwood pulp with 16% hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740 styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member is a stretch thermal laminate composed of a 17 g/m² polypropylene spunbond fabric bonded to a 17.7 g/m² co-extruded linear-low-density-polyethylene film having a 2.5% by basis weight skin layer of catalloy and ethyl vinyl acetate (available from Kimberly-Clark Corporation located in Dallas, Tex.).

EXAMPLE 9

In Sample 9, the topsheet layer was a 17 g/m² polypropylene spunbond nonwoven fabric treated for wettability with AHCOVEL N-62 surfactant. This spunbond material is available from Kimberly-Clark located in Dallas, Tex. The absorbent, retention portion was an approximately 330 g/m², air formed composite composed of 37% FAVOR SXM 880 superabsorbent particles (available from Stockhausen Inc. located in Greensboro, S.C.), and 63% softwood pulp with 16% hardwood (available from U.S. Alliance Forest Products located in Coosa River, Ala. under the designation CR 1654). The air formed composite was formed onto a 17 g/m² cellulosic wetlaid tissue. This tissue was included as part of the absorbent, retention portion during testing. The outer cover, backsheet member about 16 g/m² of PEBAX 3533 cast film (available from AtoChem of Philadelphia, Pa.) which was laminated to a 27 g/m², biax point-bonded polyethylene polypropylene, side by side bicomponent, spunbond fibrous web with 2 g/m² of H2525A adhesive (available from AtoFindley Adhesive, in Milwaukee, Wis.).

EXAMPLE 10

In Sample 10, the topsheet layer was a 17 g/m² polypropylene spunbond nonwoven fabric treated for wettability with AHCOVEL N-62 surfactant. This spunbond material is available from Kimberly-Clark located in Dallas, Tex. The absorbent, retention portion was an approximately 330 g/m² air formed composite composed of 37% FAVOR SXM 880 superabsorbent particles (available from Stockhausen Inc. located in Greensboro, S.C.), and 63% softwood pulp with 16% hardwood (available from U.S. Alliance Forest Products located in Coosa River, Ala. under the designation CR 1654). The air formed composite was formed onto a 17 g/m² cellulosic wetlaid tissue. This tissue was included as part of the absorbent, retention portion during testing. The outer cover, backsheet member included 14 g/m² of strands composed of KRATON G2760 elastomeric resin (available from Shell Chemical Company) laminated with 0.3 g/m² of H2525A adhesive (available from AtoFindley Adhesive) between two facings, each facing composed of a 24 g/m² point bonded bicomponent spunbond fabric. The strands were distributed with about 12 strands per inch (2.54 cm) of sample width.

EXAMPLE 11

In Sample 11, the topsheet layer was a 17 g/m² polypropylene spunbond nonwoven fabric treated for wettability with AHCOVEL N-62 surfactant. This spunbond material is available from Kimberly-Clark located in Dallas, Tex. The absorbent, retention portion was an approximately 455 g/m² composite composed of about 259 g/m² of SAICCOR 94 eucalyptus pulp (available from Central National-Gottesman, Inc. located in Purchase, N.Y.); 173 g/m² of FAVOR SXM 880 superabsorbent particles available from Stockhausen Inc. located in Greensboro, S.C.); and 23 g/m² of KRATON G2740 styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member included 14 g/m² of strands composed of KRATON G2760 elastomeric resin (available from Shell Chemical Company) laminated with 0.3 g/m² of H2525A adhesive (available from AtoFindley Adhesive), between two facings, each facing composed of a 24 g/m², point bonded bicomponent spunbond fabric. The strands were distributed with about 12 strands per inch (2.54 cm) of sample width.

EXAMPLE 12

In Sample 12, the top sheet was a 17 g/m² polypropylene spunbond nonwoven fabric treated for wettability with AHCOVEL N-62 surfactant. This spunbond material is available from Kimberly-Clark located in Dallas, Tex. The absorbent, retention portion was an approximately 330 g/m² composite composed of about 126 g/m² of softwood pulp with 16% hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740 styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member included 14 g/m² of strands composed of KRATON G2760 elastomeric resin (available from Shell Chemical Company) laminated with 0.3 g/m² of H2525A adhesive (available from AtoFindley Adhesive) between two facings, each facing composed of a 24 g/m² point bonded bicomponent spunbond fabric. The strands were distributed with about 12 strands per inch (2.54 cm) of sample width.

Example 13

In Sample 13, the topsheet layer was a 17 g/m² polypropylene spunbond nonwoven fabric treated for wettability with AHCOVEL N-62 surfactant. This spunbond material is available from Kimberly-Clark located in Dallas, Tex. The absorbent, retention portion included two layers. Each layer was an approximately 330 g/m² composite composed of about 126 g/m² softwood pulp with 16% hardwood (available from U.S. Alliance Forest Products located in Coosa River, Ala. under the designation CR 1654); 70 g/m² of FAVOR SXM 880 superabsorbent particles (available from Stockhausen Inc. located in Greensboro, S.C.); and 134 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member included 14 g/m² of strands composed of KRATON G2760 elastomeric resin (available from Shell Chemical Company) laminated with 0.3 g/m² of H2525A adhesive (available from AtoFindley Adhesive) between two facings, each facing composed of a 24 g/m² point bonded bicomponent spunbond fabric. The strands were distributed with about 12 strands per inch (2.54 cm) of sample width.

EXAMPLE 14

In Sample 14, the top sheet was a 17 g/m² polypropylene spunbond nonwoven fabric treated for wettability with AHCOVEL N-62 surfactant. This spunbond material is available from Kimberly-Clark located in Dallas, Tex. The absorbent, retention portion was an approximately 330 g/m² air formed composite composed of 37% FAVOR SXM 880 superabsorbent particles (available from Stockhausen Inc. located in Greensboro, S.C.), and 63% softwood pulp with 16% hardwood (available from U.S. Alliance Forest Products located in Coosa River, Ala. under the designation CR 1654). The air formed composite was formed onto a 17 g/m² cellulosic wetlaid tissue. This tissue was included as part of the absorbent, retention portion during testing. The outer cover, backsheet member was a stretch thermal laminate composed of a 17 g/m² polypropylene spunbond fabric bonded to a 17.7 g/m², co-extruded linear-low-density-polyethylene film having a 2.5% by basis weight skin layer of catalloy and ethyl vinyl acetate (available from Kimberly-Clark Corporation located in Dallas, Tex.).

EXAMPLE 15

Sample 15 represents a comparative diaper corresponding to the type manufactured Jul. 20, 1998 by Kimberly-Clark Corporation under the name STEP 3 HUGGIES SUPREME diapers. The sample contained a nonwoven, liquid pervious topsheet layer; a superabsorbent and pulp, airformed absorbent retention portion wrapped in cellulosic tissues; and a liquid impermeable outercover, backsheet member composed of spunbond-meltblown-spunbond (SMS) composite, nonwoven fabric laminated to a polymer film.

EXAMPLE 16

Sample 16 represents a comparative diaper corresponding to the type manufactured May 19, 1998 by Kimberly-Clark Corporation under the name STEP 3 HUGGIES ULTRATRIM diapers. The sample contained a nonwoven, liquid pervious topsheet layer; a superabsorbent and pulp, airformed absorbent retention portion wrapped in cellulosic tissues; and a liquid impermeable outercover, backsheet member composed of thermally bonded spunbond nonwoven fabric laminated to a polymer film.

EXAMPLE 17

Sample 17 represents a comparative diaper corresponding to the type manufactured Mar. 2, 1998 by Proctor and Gamble Company under the name PAMPERS BABY DRY diapers, size 3.

EXAMPLE 18

Sample 18 represents a comparative diaper corresponding to the type manufactured Apr. 19, 1998 by Proctor and Gamble Company under the name PAMPERS PREMIUM diapers, size 3.

EXAMPLE 19

Sample 19 represents a comparative training pant corresponding to the type manufactured Oct. 23, 1997 by Kimberly-Clark Corporation under the name PULL-UPS medium Girl training pants. The example contained a nonwoven, liquid pervious topsheet layer; a superabsorbent and pulp, airformed absorbent retention portion wrapped in cellulosic tissues; and a liquid impermeable outer cover, backsheet member composed of a polymer film adhesively laminated to a nonwoven spunbond fabric.

EXAMPLE 20

Sample 20 represents a comparative training pant corresponding to the type manufactured Jun. 10, 1998 by Kimberly-Clark Corporation under the name PULL-UPS medium Boy training pants. The example contained a nonwoven, liquid pervious topsheet layer; a superabsorbent and pulp, airformed absorbent retention portion wrapped in cellulosic tissues; and a liquid impermeable outer cover, backsheet member composed of a polymer film adhesive laminated to a nonwoven spunbond fabric.

EXAMPLE 21

Sample 21 represents a comparative training pant corresponding to the type manufactured Jul. 25, 1997 by SCA Molnlycke under the name UP & GO LIBERO for girls.

EXAMPLE 22

Sample 22 represents a comparative training pant corresponding to the type manufactured Jun. 4, 1997 by SCA Molnlycke under the name UP & GO LIBERO for boys.

The properties of the samples from Examples 1 through 22 are summarized in the following TABLE 1. Samples 1 through 22 did not include configurations which met the requirements of the invention.

TABLE 1

| Sample No. | Article Elongation at Peak Load % | Article Elongation at 100 g % |
|---|---|---|
| 1 | 26.90 | 1.62 |
| 1 | 29.90 | 2.37 |
| 1 | 32.40 | 2.87 |
| 1-Average | 29.73 | 2.29 |
| 2 | 28.40 | 2.53 |
| 2 | 28.30 | 2.40 |
| 2 | 30.00 | 1.74 |
| 2-Average | 28.90 | 2.22 |
| 3 | 29.00 | 2.59 |
| 3 | 31.10 | 2.83 |
| 3 | 31.70 | 4.61 |
| 3-Average | 30.60 | 3.34 |
| 4 | 31.40 | 3.83 |
| 4 | 32.90 | 3.67 |
| 4 | 27.80 | 2.18 |
| 4-Average | 30.70 | 3.23 |
| 5 | 30.50 | 1.71 |
| 5 | 29.30 | 1.02 |
| 5 | 29.40 | 1.67 |
| 5-Average | 29.73 | 1.46 |
| 6 | 27.70 | 1.51 |
| 6 | 30.40 | 1.13 |
| 6 | 23.70 | 1.08 |
| 6-Average | 27.27 | 1.24 |
| 7 | 29.80 | 2.56 |
| 7 | 30.60 | 1.37 |
| 7 | 26.60 | 2.69 |
| 7-Average | 29.00 | 2.21 |
| 8 | 29.20 | 1.57 |
| 8 | 25.60 | 1.48 |
| 8 | 24.00 | 0.91 |
| 8-Average | 26.27 | 1.32 |
| 9 | 30.70 | 1.18 |
| 9 | 28.80 | 1.68 |
| 9 | 29.70 | 1.59 |
| 9-Average | 29.73 | 1.48 |
| 10 | 29.80 | 0.84 |
| 10 | 25.90 | 0.75 |
| 10 | 27.70 | 0.80 |
| 10-Average | 27.80 | 0.80 |
| 11 | 33.10 | 1.90 |
| 11 | 30.30 | 1.43 |
| 11 | 30.30 | 2.10 |
| 11-Average | 31.23 | 1.81 |
| 12 | 29.20 | **** |
| 12 | 30.20 | 1.22 |
| 12 | 35.60 | 1.66 |
| 12-Average | 31.67 | 1.44 |
| 13 | 44.80 | 1.01 |
| 13 | 27.50 | 1.74 |
| 13 | 45.10 | 1.88 |
| 13-Average | 39.13 | 1.54 |
| 14 | 23.30 | 1.22 |
| 14 | 25.10 | 0.84 |
| 14 | 28.40 | 0.87 |
| 14-Average | 25.60 | 0.98 |
| 15 | 24.20 | 2.86 |
| 15 | 28.70 | 2.20 |
| 15 | 26.70 | 2.61 |
| 15-Average | 26.53 | 2.56 |
| 16 | 27.70 | 2.03 |
| 16 | 32.90 | 3.52 |
| 16 | 19.30 | 1.78 |
| 16-Average | 26.63 | 2.44 |
| 17 | 16.40 | 2.12 |
| 17 | 14.90 | 2.29 |
| 17 | 42.30 | 2.89 |
| 17-Average | 24.53 | 2.43 |
| 18 | 43.30 | 1.75 |
| 18 | 29.20 | 2.01 |
| 18 | 26.80 | 1.63 |
| 18-Average | 33.10 | 1.80 |
| 19 | 34.70 | 4.52 |
| 19 | 29.80 | 3.23 |
| 19 | 36.10 | 3.21 |

TABLE 1-continued

| Sample No. | Article Elongation at Peak Load % | Article Elongation at 100 g % |
|---|---|---|
| 19-Average | 33.53 | 3.65 |
| 20 | 31.80 | 2.22 |
| 20 | 32.10 | 2.44 |
| 20 | 31.90 | 4.51 |
| 20-Average | 31.93 | 3.06 |
| 21 | 33.80 | 2.97 |
| 21 | 47.20 | 1.43 |
| 21 | 40.50 | 2.11 |
| 21-Average | 40.50 | 2.17 |
| 22 | 37.40 | 1.80 |
| 22 | 27.50 | 3.61 |
| 22 | 45.60 | 1.68 |
| 22-Average | 36.83 | 2.37 |

***Specimen broke prior to reaching 100 g

Each of the following samples was composed of a stretchable, absorbent retention portion which was sandwiched and held between a stretchable, liquid-permeable topsheet layer, and a stretchable, substantially liquid-impermeable outer cover, backsheet member.

EXAMPLE 23

In Sample 23, the topsheet layer was a nonwoven, spunbond polypropylene fabric composed of about 2 to 3 denier fibers formed into a web. The web had a basis weight of about 12 g/m², and was necked approximately 60%. About 9 g/m² of strand material composed of KRATON G2760 elastomer (available from Shell Chemical Company located in Houston, Tex.) were adhered to the necked spunbond material at a distribution of about eight strands per inch (2.54 cm). The fabric was surface treated with an AHCOVEL surfactant wettability package from ICI Americas, Inc. of Wilmington, Del. at a 0.6 wt % add-on level. The absorbent, retention portion was a 555 g/m², homogeneous composite composed of about 252 g/m² of softwood pulp with 16% hardwood (available from U.S. Alliance Forest Products located in Coosa River, Ala. under the designation CR 1654); 148 g/m² of FAVOR SXM 880 superabsorbent particles (available from Stockhausen Inc. located in Greensboro, S.C.); and 155 g/m² of KRATON G2740, styrene-butadiene block copolymer elastomeric resin (available from Shell Chemical Company located in Houston, Tex.). The absorbent was surface treated with a 3% solution of a 3:1 ratio (by active weight) of AHCOVEL N62 surfactant (available from ICI Americas, Inc. of Wilmington, Del.) and GLUCOPON 220UP surfactant (available from Henkel Corporation—Emery Group located in Cincinnati, Ohio). The outer cover, backsheet member was composed of about 16 g/m² of a PEBAX 3533 cast elastomer film (available from AtoChem of Philadelphia, Pa.) which was laminated to a 0.8 osy (27.1 g/m²) biax point-bonded, polyethylene-polypropylene, side-by-side bicomponent spunbond fibrous web with 2 g/m² of H2525A adhesive (available from AtoFindley Adhesive located in Milwaukee, Wis.).

EXAMPLE 24

In Sample 24, the top sheet was composed of a 33.9 g/m², side-by-side polypropylene flexible polyolefin bicomponent, point bonded, spunbond nonwoven fibrous web. The fabric was surface treated with a wettability package, such as the package available from ICI Americas located in Wilmington, Delaware under the tradename AHCOVEL. The absorbent, retention portion was a 555 g/m² homogeneous composite composed of about 252 g/m² of softwood pulp with 16% hardwood (available from U.S. Alliance Forest Products located in Coosa River, Ala. under the designation CR 1654); 148 g/m² of FAVOR SXM 880 superabsorbent particles (available from Stockhausen Inc. located in Greensboro, S.C.); and 155 g/m² of a KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was composed of about 16 g/m² of PEBAX 3533 cast film (available from AtoChem of Philadelphia, Pa.) which was laminated to a 0.8 osy (27.1 g/m²) biax point-bonded polyethylene-polypropylene, side-by-side bicomponent, spunbond fibrous web with 2 g/m² of H2525A adhesive (available from AtoFindley Adhesive, in Milwaukee, Wis.).

EXAMPLE 25

In Sample 25, the top sheet was a nonwoven, spunbond polypropylene fabric composed of approximately 2 to 3 denier fibers formed into a web, which had a basis weight of about 12 g/m² and was necked approximately 60%. About 9 g/m² of strand material composed of KRATON G2760 elastomer were adhered to the necked spunbond material with a distribution of approximately eight strands per inch (2.54 cm). The fabric was surface treated with AHCOVEL surfactant at a 0.6 wt % add-on level. The absorbent, retention portion was an approximately 485 g/m² composite composed of about 252 g/m² softwood pulp with 16% hardwood (available from U.S. Alliance Forest Products located in Coosa River, Ala. under the designation CR 1654); 148 g/m² of FAVOR SXM 880 superabsorbent particles (available from Stockhausen Inc. located in Greensboro, S.C.); and 85 g/m² of a KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was composed of about 16 g/m² of PEBAX 3533 cast film (available from AtoChem of Philadelphia, Pa.) which was laminated to a 0.8 osy (27.1 g/m²) biax point-bonded polyethylene-polypropylene, side-by-side bicomponent spunbond fibrous web with 2 g/m² of H2525A adhesive (available from AtoFindley Adhesive located in Milwaukee, Wis.).

EXAMPLE 26

In Sample 26, the top sheet was composed of a 33.9 g/m², side-by-side polypropylene flexible polyolefin bicomponent, point bonded, spunbond nonwoven fibrous web. The fabric was surface treated with a wettability package such as that available from ICI Americas located in Wilmington, Del. under the tradename AHCOVEL. The absorbent, retention portion was a 485 g/m² composite composed of about 252 g/m² of softwood pulp with 16% hardwood (available from U.S. Alliance Forest Products located in Coosa River, Ala. under the designation CR 1654); 148 g/m² of FAVOR SXM 880 superabsorbent particles; and 85 g/m² of a KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was composed of about 16 g/m² of a PEBAX 3533 cast film (available from AtoChem of Philadelphia, Pa.) which was laminated to a 0.8 osy (27.1 g/m$^2$) biax point-bonded polyethylene-polypropylene, side-by-side bicomponent, spunbond fibrous web with 2 g/m$^2$ of H2525A adhesive (available from AtoFindley Adhesive).

EXAMPLE 27

In Sample 27, the topsheet layer was a nonwoven, spunbond polypropylene fabric composed of about 2 to 3 denier fibers formed into a web, which had a basis weight of about 12 g/m$^2$ and was necked approximately 60%. About 9 g/m$^2$ of KRATON G2760, elastic strand material were adhered to the necked spunbond material and distributed with about eight strands per inch (2.54 cm). The fabric was surface treated with an AHCOVEL surfactant wettability package available from ICI Americas, Inc. of Wilmington, Del. at a 0.6 wt % add-on level. The absorbent, retention portion was a 555 g/m$^2$ homogeneous composite composed of about 252 g/m$^2$ softwood pulp with 16% hardwood (available from U.S. Alliance Forest Products located in Coosa River, Ala. under the designation CR 1654); 148 g/m$^2$ of FAVOR SXM 880 superabsorbent particles (available from Stockhausen Inc. located in Greensboro, S.C.); and 155 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member included 14 g/m$^2$ of strands composed of KRATON G2760 elastomeric resin (available from Shell Chemical Company) laminated with 0.3 g/m$^2$ of H2525A adhesive (available from AtoFindley Adhesive) between two facings, with each facing composed of a 24 g/m$^2$, point bonded bicomponent spunbond fabric. The strands were distributed with 12 strands per inch (2.54 cm) of sample width.

EXAMPLE 28

In Sample 28, the top sheet was composed of a 33.9 g/m$^2$, side-by-side polypropylene flexible polyolefin bicomponent, point bonded, spunbond nonwoven fibrous web. The fabric was surface treated with a wettability package such as that available from ICI Americas under the tradename AHCOVEL. The absorbent, retention portion was a 555 g/m$^2$ homogeneous composite composed of about 252 g/m$^2$ softwood pulp with 16% hardwood (available from U.S. Alliance Forest Products located in Coosa River, Ala. under the designation CR 1654); 148 g/m$^2$ of FAVOR SXM 880 superabsorbent particles (available from Stockhausen Inc.); and 155 g/m$^2$ of KRATON G2740, styrene-butadiene block copolymer elastomeric resin(available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member was composed of 14 g/m$^2$ of KRATON G2760 elastomeric resin strands laminated with 0.3 g/m$^2$ of H2525A adhesive (available from AtoFindley Adhesive) between two facings, with each facing composed of a 24 g/m$^2$, point bonded, bicomponent spunbond fabric. The elastomeric resin strands were distributed with about 12 strands per inch (2.54 cm) of sample width.

EXAMPLE 29

In Sample 29, the topsheet layer was a nonwoven, spunbond polypropylene fabric composed of approximately 2 to 3 denier fibers formed into a web which had a basis weight of about 12 g/m$^2$ and was necked approximately 60%. About 9 g/m$^2$ of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion was a 485 g/m$^2$ composite composed of about 252 g/m$^2$ softwood pulp with 16% hardwood (available from U.S. Alliance Forest Products located in Coosa River, Ala. under the designation CR 1654); 148 g/m$^2$ of FAVOR SXM 880 superabsorbent particles available from Stockhausen Inc.); and 85 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member was composed of 14 g/m$^2$ of KRATON G2760, elastomeric resin strands which were laminated with 0.3 g/m$^2$ of H2525A adhesive (available from AtoFindley Adhesive) between two facings, with each facing composed of a 24 g/m$^2$, point bonded, bicomponent spunbond fabric. The strands were distributed with about 12 strands per inch (2.54 cm) of sample width.

EXAMPLE 30

In Sample 30, the top sheet was composed of a 33.9 g/m$^2$, side-by-side polypropylene flexible polyolefin bicomponent, point bonded, spunbond nonwoven fibrous web. The fabric was surface treated with a wettability package such as that available from ICI Americas under the tradename AHCOVEL. The absorbent, retention portion was a 485 g/m$^2$ composite composed of about 252 g/m$^2$ of softwood pulp with 16% hardwood (available from U.S. Alliance Forest Products located in Coosa River, Ala. under the designation CR 1654); 148 g/m$^2$ of FAVOR SXM 880 superabsorbent particles (available from Stockhausen Inc.); and 85 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member included 14 g/m$^2$ of strands composed of KRATON G2760 elastomeric resin (available from Shell Chemical Company) which were laminated with 0.3 g/m$^2$ of H2525A adhesive (available from AtoFindley Adhesive) between two facings with each facing composed of a 24 g/m$^2$, point bonded, bicomponent spunbond fabric. The strands were distributed with about 12 strands per inch (2.54 cm) of sample width.

EXAMPLE 31

In Sample 31, the top sheet was a nonwoven, spunbond polypropylene fabric composed of approximately 2 to 3 denier fibers formed into a web which had a basis weight of about 12 g/m$^2$ and was necked approximately 60%. About 9 g/m$^2$ of KRATON G2760, strand material were adhered to the necked spunbond material and distributed with about eight strands per inch (2.54 cm). The fabric was surface treated with ACHOVEL surfactant at a 0.6 wt % add-on level. The absorbent, retention portion was a 455 g/m$^2$ composite composed of about 259 g/m$^2$ of SAICCOR 94 eucalyptus pulp (available from Central National-Gottesman, Inc. located in Purchase, N.Y.); 173 g/m$^2$ of FAVOR SXM 880 superabsorbent particles (available from Stockhausen Inc.); and 23 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was composed of about 16 g/m$^2$ of PEBAX 3533 cast film (available from AtoChem of Philadelphia, Pa.) which was laminated to a 0.8 osy (27.1 g/m$^2$) biax point-bonded, polyethylene-polypropylene, side-by-side bicomponent, spunbond fibrous web with 2 g/m$^2$ of H2525A adhesive (available from AtoFindley Adhesive located in Milwaukee, Wis.).

EXAMPLE 32

In Sample 32, the top sheet was a nonwoven, spunbond polypropylene fabric composed of about 2 to 3 denier fibers formed into a web which had a basis weight of about 12 g/m$^2$ and was necked approximately 60%. About 9 g/m$^2$ of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion was a 455 g/m$^2$ composite composed of about 259 g/m$^2$ of SAICCOR 94 eucalyptus pulp (available from Central National-Gottesman, Inc. located in Purchase, N.Y.); 173 g/m$^2$ of FAVOR SXM 880 superabsorbent particles (available from Stockhausen Inc. located in Greensboro, S.C.); and 23 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member included 14 g/m$^2$ of strands composed of KRATON G2760, elastomeric resin (available from Shell Chemical Company) laminated with 0.3 g/m$^2$ of H2525A adhesive (available from AtoFindley Adhesive) between two facings, with each facing composed of a 24 g/m$^2$, point bonded, bicomponent spunbond fabric. The strands were distributed with about 12 strands per inch (2.54 cm) of sample width.

EXAMPLE 33

In Sample 33, the top sheet was a nonwoven, spunbond polypropylene fabric composed of about 2 to 3 denier fibers formed into a web which had a basis weight of about 12 g/m$^2$ and was necked approximately 60%. About 9 g/m$^2$ of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion was a 330 g/m$^2$ composite composed of about 126 g/m$^2$ of softwood pulp with 16% hardwood (available from U.S. Alliance Forest Products located in Coosa River, Ala. under the designation CR 1654); 70 g/m$^2$ of FAVOR SXM 880 superabsorbent particles (available from Stockhausen Inc.); and 134 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member was composed of about 16 g/m$^2$ of PEBAX 3533 cast film (available from AtoChem of Philadelphia, Pa.) which was laminated to a 0.8 osy (27.1 g/m$^2$) biax point-bonded, polyethylene-polypropylene, side-by-side bicomponent, spunbond fibrous web with 2 g/m$^2$ of H2525A adhesive (available from AtoFindley Adhesive, in Milwaukee, Wis.).

EXAMPLE 34

In Sample 34, the topsheet layer was a nonwoven, spunbond polypropylene fabric composed of about 2 to 3 denier fibers formed into a web, which had a basis weight of about 12 g/m$^2$ and was necked approximately 60%. About 9 g/m$^2$ of strand material composed of KRATON G2760 elastomer were adhered to the necked spunbond fabric and was distributed with about eight strands per inch (2.54 cm). The fabric was surface treated with AHCOVEL surfactant at a 0.6 wt % add-on level. The absorbent, retention portion was a 330 g/m$^2$ composite composed of about 126 g/m$^2$ of softwood pulp with 16% hardwood (available from U.S. Alliance Forest Products located in Coosa River, Ala. under the designation CR 1654); 70 g/m$^2$ of FAVOR SXM 880 superabsorbent particles (available from Stockhausen Inc. located in Greensboro, S.C.); and 134 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member included 14 g/m$^2$ of strands composed of KRATON G2760 elastomeric resin (available from Shell Chemical Company) laminated with 0.3 g/m$^2$ of H2525A adhesive (available from AtoFindley Adhesive) between two facings, with each facing composed of a 24 g/m$^2$, point bonded bicomponent spunbond fabric. The strands were distributed with about 12 strands per inch (2.54 cm) of sample width.

EXAMPLE 35

In Sample 35, the top sheet was a nonwoven, spunbond polypropylene fabric composed of about 2 to 3 denier fibers formed into a web which had a basis weight of about 12 g/m$^2$ and was necked approximately 60%. About 9 g/m$^2$ of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion was a 475 g/m$^2$ composite composed of about 254 g/m$^2$ of debonded softwood pulp (available from Weyerhauser, located in Federal Way, Wash., under the designation NB 405); 151 g/m$^2$ of FAVOR SXM 880 superabsorbent particles (available from Stockhausen Inc.); and 70 g/m$^2$ of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The outer cover, backsheet member included about 16 g/m$^2$ of PEBAX 3533 cast film (available from AtoChem of Philadelphia, Pa.) which is laminated to a 0.8 osy (27.1 g/m$^2$) biax point-bonded, polyethylene-polypropylene, side-by-side bicomponent, spunbond fibrous web with 2 g/m$^2$ of H2525A adhesive (available from AtoFindley Adhesive located in Milwaukee, Wis.).

EXAMPLE 36

In Sample 36, the top sheet was a nonwoven, spunbond polypropylene fabric composed of about 2 to 3 denier fibers formed into a web which had a basis weight of about 12 g/m$^2$ and was necked approximately 60%. About 9 g/m$^2$ of strand material composed of KRATON G2760 elastomer were adhered to the necked spunbond material and distributed with about eight strands per inch (2.54 cm). The fabric was surface treated with AHCOVEL surfactant at a 0.6 wt % add-on level. The absorbent, retention portion was a 475 g/m² composite composed of about 254 g/m² of NB 405, debonded softwood pulp (available from Weyerhauser); 151 g/m² of FAVOR SXM 880 superabsorbent particles (available from Stockhausen Inc.); and 70 g/m² of KRATON G2740, styrene-butadiene block copolymer elastomeric resin (available from Shell Chemical Company). The absorbent was surface treated with a 3% solution of a 3:1 ratio (by active weight) of AHCOVEL N62 and GLUCOPON 220UP surfactants. The liquid impermeable outer cover, backsheet member included 14 g/m² of strands composed of KRATON G2760 elastomeric resin (available from Shell Chemical Company) which were laminated with 0.3 g/m² of H2525A adhesive (available from AtoFindley Adhesive) between two facings, with each facing composed of a 24 g/m², point bonded, bicomponent spunbond fabric. The strands were distributed with about 12 strands per inch (2.54 cm) of sample width.

The properties of the samples from Examples 23 through 36 are summarized in the following TABLES 2 and 3. Samples 23 through 36 include configurations which are representative of the invention.

TABLE 2

| | | | Elongation at 100 g/in tensile force | | | | |
|---|---|---|---|---|---|---|---|
| Sample No. | Article % | Retention portion to Article quotient | Backsheet to Article quotient | Retention portion to Backsheet quotient | Article Elongation at Peak Load % | Article Force at 45% Elongation N/cm | Article Force at 45% Elongation gm/in |
| 23 | 4.10 | 1.71 | 3.41 | 0.50 | 233.60 | 2.25 | 583.56 |
| 23 | 5.40 | 0.88 | 13.52 | 0.07 | 236.00 | 2.46 | 638.45 |
| 23 | 3.50 | 1.67 | 16.13 | 0.10 | 203.80 | 2.77 | 718.65 |
| 23 Average | 4.33 | 1.42 | 11.02 | 0.22 | 224.47 | 2.50 | 646.89 |
| 24 | 4.40 | 1.59 | 3.18 | 0.50 | 147.30 | 2.93 | 759.86 |
| 24 | 3.80 | 1.26 | 19.21 | 0.07 | 143.30 | 2.75 | 713.37 |
| 24 | 4.20 | 1.39 | 13.44 | 0.10 | 165.50 | 2.69 | 696.60 |
| 24 Average | 4.13 | 1.41 | 11.94 | 0.22 | 152.03 | 2.79 | 723.28 |
| 25 | 4.60 | 1.79 | 3.04 | 0.59 | 225.50 | 2.15 | 555.90 |
| 25 | 7.10 | 0.85 | 10.28 | 0.08 | 161.90 | 1.76 | 455.09 |
| 25 | 6.70 | 0.91 | 8.43 | 0.11 | 246.70 | 1.85 | 480.53 |
| 25 Average | 6.13 | 1.18 | 7.25 | 0.26 | 211.37 | 1.92 | 497.17 |
| 26 | 6.50 | 1.27 | 2.15 | 0.59 | 175.80 | 2.01 | 520.08 |
| 26 | 4.60 | 1.30 | 15.87 | 0.08 | 147.10 | 2.39 | 618.52 |
| 26 | 6.80 | 0.90 | 8.30 | 0.11 | 173.00 | 2.09 | 540.69 |
| 26 Average | 5.97 | 1.16 | 8.77 | 0.26 | 165.30 | 2.16 | 559.76 |
| 27 | 4.80 | 1.46 | 16.91 | 0.09 | 232.00 | 2.12 | 548.42 |
| 27 | 3.50 | 1.36 | 21.35 | 0.06 | 241.20 | 2.27 | 589.28 |
| 27 | 4.00 | 1.46 | 17.28 | 0.08 | 246.80 | 2.08 | 537.58 |
| 27 Average | 4.10 | 1.43 | 18.51 | 0.08 | 240.00 | 2.16 | 558.43 |
| 28 | 4.50 | 1.56 | 18.04 | 0.09 | 424.20 | 2.68 | 693.59 |
| 28 | 4.40 | 1.08 | 16.98 | 0.06 | 377.70 | 2.61 | 675.97 |
| 28 | 4.00 | 1.46 | 17.28 | 0.08 | 402.30 | 2.90 | 751.50 |
| 28 Average | 4.30 | 1.37 | 17.43 | 0.08 | 401.40 | 2.73 | 707.02 |
| 29 | 5.20 | 1.58 | 15.61 | 0.10 | 245.10 | 1.50 | 388.94 |
| 29 | 8.00 | 0.75 | 9.34 | 0.08 | 228.30 | 1.39 | 360.37 |
| 29 | 6.70 | 0.91 | 10.31 | 0.09 | 245.00 | 1.57 | 407.78 |
| 29 Average | 6.63 | 1.08 | 11.75 | 0.09 | 239.47 | 1.49 | 385.70 |
| 30 | 6.40 | 1.29 | 12.68 | 0.10 | 424.30 | 2.13 | 552.05 |
| 30 | 7.30 | 0.82 | 10.23 | 0.08 | 143.00 | 1.88 | 487.70 |
| 30 | 6.30 | 0.97 | 10.97 | 0.09 | 166.20 | 2.03 | 526.08 |
| 30 Average | 6.67 | 1.03 | 11.30 | 0.09 | 244.50 | 2.01 | 521.94 |
| 31 | 4.30 | 1.31 | 3.25 | 0.40 | 226.00 | 1.26 | 327.51 |
| 31 | 4.00 | 1.26 | 18.25 | 0.07 | 221.40 | 1.52 | 393.98 |
| 31 | 3.50 | 1.00 | 16.13 | 0.06 | 164.10 | 1.25 | 323.60 |
| 31 Average | 3.93 | 1.19 | 12.54 | 0.18 | 203.83 | 1.34 | 348.36 |
| 32 | 3.60 | 1.56 | 22.55 | 0.07 | 198.10 | 1.31 | 339.67 |
| 32 | 4.50 | 1.12 | 16.60 | 0.07 | 189.50 | 1.08 | 279.35 |
| 32 | 4.20 | 0.84 | 16.45 | 0.05 | 180.90 | 1.59 | 412.91 |
| 32 Average | 4.10 | 1.17 | 18.53 | 0.06 | 189.50 | 1.33 | 343.98 |
| 33 | 4.00 | 4.24 | 3.50 | 1.21 | 212.20 | 2.06 | 532.39 |
| 33 | 3.20 | 2.58 | 22.81 | 0.11 | 249.10 | 2.31 | 598.66 |
| 33 | 4.30 | 1.03 | 13.13 | 0.08 | 255.70 | 2.15 | 558.21 |
| 33 Average | 3.83 | 2.62 | 13.14 | 0.47 | 239.00 | 2.17 | 563.09 |
| 34 | 9.30 | 1.82 | 8.73 | 0.21 | 233.20 | 1.48 | 384.33 |

TABLE 2-continued

| | | Elongation at 100 g/in tensile force | | | | | |
|---|---|---|---|---|---|---|---|
| Sample No. | Article % | Retention portion to Article quotient | Backsheet to Article quotient | Retention portion to Backsheet quotient | Article Elongation at Peak Load % | Article Force at 45% Elongation N/cm | Article Force at 45% Elongation gm/in |
| 34 | 8.60 | 0.96 | 8.69 | 0.11 | 230.80 | 1.62 | 418.93 |
| 34 | 8.20 | 0.54 | 8.43 | 0.06 | 230.00 | 1.61 | 415.93 |
| 34 | 8.70 | 1.11 | 8.61 | 0.13 | 231.33 | 1.57 | 406.40 |
| 34 Average | | | | | | | |
| 35 | 5.30 | 2.00 | 2.64 | 0.76 | 244.30 | 1.58 | 409.62 |
| 35 | 7.00 | 1.68 | 10.43 | 0.16 | 236.00 | 1.29 | 332.96 |
| 35 | 6.20 | 2.04 | 9.10 | 0.22 | 224.60 | 1.42 | 368.06 |
| 35 Average | 6.17 | 1.91 | 7.39 | 0.38 | 234.97 | 1.43 | 370.21 |
| 36 | 7.70 | 1.38 | 10.54 | 0.13 | 236.50 | 1.07 | 278.16 |
| 36 | 8.50 | 1.38 | 8.79 | 0.16 | 237.10 | 0.96 | 247.50 |
| 36 | 8.80 | 1.44 | 7.85 | 0.18 | 246.50 | 1.13 | 292.44 |
| 36 Average | 8.33 | 1.40 | 9.06 | 0.16 | 240.03 | 1.05 | 272.70 |

TABLE 3

| | Tensile force at 15% Elongation | | | | |
|---|---|---|---|---|---|
| Sample No. | Article N/cm | Article gram/in | Retention portion to article quotient | Backsheet to article quotient | Retention portion to backsheet quotient |
| 23 | 1.43 | 371.20 | 0.64 | 0.28 | 2.28 |
| 23 | 1.26 | 325.30 | 0.97 | 0.09 | 10.75 |
| 23 | 1.84 | 477.90 | 0.65 | 0.08 | 8.37 |
| 23 Average | 1.51 | 391.47 | 0.75 | 0.15 | 7.13 |
| 24 | 1.41 | 364.00 | 0.66 | 0.29 | 2.28 |
| 24 | 1.51 | 391.30 | 0.81 | 0.08 | 10.75 |
| 24 | 1.74 | 450.20 | 0.69 | 0.08 | 8.37 |
| 24 Average | 1.55 | 401.83 | 0.72 | 0.15 | 7.13 |
| 25 | 1.23 | 318.40 | 0.59 | 0.33 | 1.80 |
| 25 | 0.88 | 227.70 | 1.13 | 0.13 | 8.77 |
| 25 | 0.90 | 234.10 | 0.94 | 0.16 | 5.94 |
| 25 Average | 1.00 | 260.07 | 0.89 | 0.21 | 5.50 |
| 26 | 0.92 | 238.40 | 0.79 | 0.44 | 1.80 |
| 26 | 1.25 | 323.80 | 0.80 | 0.09 | 8.77 |
| 26 | 0.93 | 242.10 | 0.91 | 0.15 | 5.94 |
| 26 Average | 1.03 | 268.10 | 0.83 | 0.23 | 5.50 |
| 27 | 1.25 | 323.30 | 0.74 | 0.13 | 5.88 |
| 27 | 1.59 | 413.20 | 0.76 | 0.09 | 8.16 |
| 27 | 1.30 | 336.90 | 0.92 | 0.12 | 7.69 |
| 27 Average | 1.38 | 357.80 | 0.81 | 0.11 | 7.24 |
| 28 | 1.43 | 369.80 | 0.65 | 0.11 | 5.88 |
| 28 | 1.40 | 362.20 | 0.87 | 0.11 | 8.16 |
| 28 | 1.69 | 436.60 | 0.71 | 0.09 | 7.69 |
| 28 Average | 1.50 | 389.53 | 0.74 | 0.10 | 7.24 |
| 29 | 1.03 | 266.00 | 0.71 | 0.15 | 4.64 |
| 29 | 0.72 | 185.60 | 1.39 | 0.21 | 6.66 |
| 29 | 0.85 | 220.60 | 1.00 | 0.18 | 5.46 |
| 29 Average | 0.86 | 224.07 | 1.03 | 0.18 | 5.59 |
| 30 | 1.04 | 269.80 | 0.70 | 0.15 | 4.64 |
| 30 | 0.92 | 237.20 | 1.09 | 0.16 | 6.66 |
| 30 | 1.06 | 275.80 | 0.80 | 0.15 | 5.46 |
| 30 Average | 1.01 | 260.93 | 0.86 | 0.15 | 5.59 |
| 31 | 1.48 | 382.80 | 0.76 | 0.27 | 2.78 |
| 31 | 1.63 | 422.50 | 0.67 | 0.07 | 9.56 |
| 31 | 1.48 | 382.30 | 0.81 | 0.10 | 8.39 |
| 31 | 1.53 | 395.87 | 0.75 | 0.15 | 6.91 |
| 31 Average | | | | | |
| 32 | 1.48 | 384.60 | 0.76 | 0.11 | 7.18 |
| 32 | 1.22 | 316.90 | 0.89 | 0.12 | 7.26 |
| 32 | 1.63 | 422.90 | 0.73 | 0.10 | 7.70 |
| 32 | 1.45 | 374.80 | 0.79 | 0.11 | 7.38 |
| 32 Average | | | | | |
| 33 | 1.32 | 341.90 | 0.25 | 0.31 | 0.83 |
| 33 | 1.48 | 383.20 | 0.44 | 0.08 | 5.71 |
| 33 | 1.32 | 341.00 | 0.78 | 0.11 | 7.19 |
| 33 | 1.37 | 355.37 | 0.49 | 0.16 | 4.57 |
| 33 Average | | | | | |
| 34 | 0.63 | 163.60 | 0.53 | 0.25 | 2.14 |
| 34 | 0.70 | 182.40 | 0.92 | 0.21 | 4.33 |
| 34 | 0.71 | 183.60 | 1.45 | 0.22 | 6.60 |
| 34 | 0.68 | 176.53 | 0.97 | 0.23 | 4.36 |
| 34 Average | | | | | |
| 35 | 1.04 | 268.40 | 0.51 | 0.39 | 1.31 |
| 35 | 0.81 | 211.00 | 0.60 | 0.14 | 4.28 |
| 35 | 0.91 | 234.50 | 0.51 | 0.16 | 3.21 |
| 35 | 0.92 | 237.97 | 0.54 | 0.23 | 2.93 |
| 35 Average | | | | | |
| 36 | 0.70 | 180.60 | 0.76 | 0.23 | 3.38 |
| 36 | 0.65 | 169.20 | 0.74 | 0.23 | 3.25 |
| 36 | 0.67 | 172.90 | 0.69 | 0.23 | 2.95 |
| 36 | 0.67 | 174.23 | 0.73 | 0.23 | 3.19 |
| 36 Average | | | | | |

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal direction, a transverse direction, a front portion, a back portion, and an intermediate portion interconnecting said front and back portions, said article comprising:

a substantially elastomerically stretchable backsheet member;

a liquid-permeable topsheet layer; and a substantially elastomerically stretchable retention portion sandwiched between said backsheet member and said topsheet layer;

wherein said absorbent article provides a composite-article, elongation-at-peak-load value which is at least about 50%.

2. An article as recited in claim 1, wherein said topsheet layer is substantially elastomerically stretchable.

3. An article as recited in claim 1, wherein said article provides composite-article tensile load force value of not more than about 750 gram-force per inch of specimen width at a composite-article elongation of 45%.

4. An article as recited in claim 1, wherein said article provides an article elongation of at least about 4% when subjected to a tensile force of 100 gram-force per inch of specimen width.

5. An article as recited in claim 1, wherein a quotient of an elongation value of said backsheet member divided by said composite-article elongation value of said article is at least about 1.1, where each elongation value is determined at a loading of 100 gram-force per inch of specimen width.

6. An article as recited in claim 5, wherein said quotient of said elongation value of said backsheet member divided by composite-article elongation value of said article is not more than about 20, where each elongation value is determined at said loading of 100 gram-force per inch of specimen width.

7. An article as recited in claim 1, wherein a quotient of an elongation value of said retention portion divided by said composite-article elongation value of said article is at least about 1.01, where each elongation value is determined at a loading of 100 g/inch.

8. An article as recited in claim 7, wherein said quotient of said elongation value of said retention portion divided by said composite-article elongation value of said article is not more than about 5, where each elongation value is determined at said loading of 100 gram-force per inch of specimen width.

9. An article as recited in claim 1, wherein a quotient of an elongation value of said retention portion divided by an elongation value of said backsheet member is at least about 0.06, where each elongation value is determined at a loading of 100, gram-force per inch of specimen width.

10. An article as recited in claim 9, wherein said quotient of said elongation value of said retention portion divided by said elongation value of said backsheet member is not more than about 0.95, where each elongation value is determined at said loading of 100 gram-force per inch of specimen width.

11. An article as recited in claim 1, wherein a quotient of a tensile force in said backsheet member, at a 15% backsheet elongation, divided by a composite-article tensile force in said article, at a 15% article elongation, is at least about 0.05.

12. An article as recited in claim 11, wherein said quotient of said tensile force in said backsheet member, at the 15% backsheet elongation, divided by said composite-article tensile force in said article, at the 15% article elongation, is not more than about 0.9.

13. An article as recited in claim 1, wherein a quotient of a tensile force in said retention portion, at a 15% retention portion elongation, divided by a composite-article tensile force in said article, at a 15% article elongation, is at least about 0.1.

14. An article as recited in claim 13, wherein said quotient of said tensile force in said retention portion, at the 15% retention portion elongation, divided by said composite-article tensile force in said article, at the 15% article elongation, is not more than about 0.99.

15. An article as recited in claim 1, wherein a quotient of a tensile force in said retention portion, at a 15% retention portion elongation, divided by a tensile force in said backsheet member, at a 15% backsheet elongation, is at least about 1.5.

16. An article as recited in claim 15, wherein said quotient of said tensile force in said retention portion, at the 15% retention portion elongation, divided by said tensile force in said backsheet member, at the 15% backsheet elongation, is not more than about 8.

* * * * *

UNITED STATES PATENT AND TRADEMARK OFFICE
CERTIFICATE OF CORRECTION

PATENT NO.    : 6,231,557 B1                                          Page 1 of 1
DATED         : May 15, 2001
INVENTOR(S)   : Candace Dyan Krautkramer et al.

It is certified that error appears in the above-identified patent and that said Letters Patent is hereby corrected as shown below:

Column 10,
Line 12, delete "900°" and substitute -- 90° --.

Column 51,
Line 34, delete "g/inch", and subtitute -- gram-force per inch of specimen width --.

Signed and Sealed this

Twelfth Day of March, 2002

Attest:

JAMES E. ROGAN
Attesting Officer
Director of the United States Patent and Trademark Office